US010603202B1

(12) United States Patent
Fried

(10) Patent No.: US 10,603,202 B1
(45) Date of Patent: Mar. 31, 2020

(54) SPLINT AND METHOD OF USE

(71) Applicant: Scott Fried, Gwynedd Valley, PA (US)

(72) Inventor: Scott Fried, Gwynedd Valley, PA (US)

(*) Notice: Subject to any disclaimer, the term of this patent is extended or adjusted under 35 U.S.C. 154(b) by 450 days.

(21) Appl. No.: 15/450,286

(22) Filed: Mar. 6, 2017

Related U.S. Application Data

(63) Continuation-in-part of application No. 14/663,626, filed on Mar. 20, 2015, now Pat. No. 9,895,251, and a continuation-in-part of application No. 29/580,387, filed on Oct. 7, 2016, now Pat. No. Des. 824,527.

(51) Int. Cl.
*A61F 5/058* (2006.01)
*A61F 5/048* (2006.01)

(52) U.S. Cl.
CPC .......... *A61F 5/048* (2013.01); *A61F 5/05866* (2013.01)

(58) Field of Classification Search
CPC .... A61F 5/0118; A61F 5/013; A61F 5/05866; A61F 5/05875; A61F 2005/0186; A61F 2007/0035; A61F 2007/0036; A61F 13/104; A61F 13/107; A61F 2007/0037; A61F 2/586; A61F 5/00; A61F 5/01; A61F 13/041; A61F 5/10; A61F 5/019; A61F 13/105; A61F 2002/587; A61F 2007/0038; A61F 5/05841; A61F 5/04; A61F 13/04; A61H 1/0288; A61H 1/0285; A63B 23/16; A63B 21/4025; A63B 21/4019; A63B 21/0552; A63B 21/4021; A63B 21/023; A63B 21/4017; A63B 23/14; A63B 69/0059; A41D 13/087; A41D 19/01588; A41D 13/088; A41D 2500/10; A61B 2017/00902; A61B 19/00
See application file for complete search history.

(56) References Cited

U.S. PATENT DOCUMENTS

| | | | | |
|---|---|---|---|---|
| 4,602,620 A | * | 7/1986 | Marx | A61F 5/10 602/21 |
| 4,765,320 A | * | 8/1988 | Lindemann | A61F 5/0118 602/22 |
| 4,790,300 A | * | 12/1988 | Marx | A61F 5/013 602/21 |
| 4,862,877 A | * | 9/1989 | Barber | A61F 5/05866 602/22 |
| 5,254,078 A | * | 10/1993 | Carter | A61F 5/013 602/16 |
| 6,093,162 A | * | 7/2000 | Fairleigh | A61F 5/013 602/22 |

* cited by examiner

*Primary Examiner* — Ophelia A Hawthorne
(74) *Attorney, Agent, or Firm* — Garcia-Zamor Intellectual Property Law, LLC; Ruy Garcia-Zamor

(57) ABSTRACT

A splint for facilitating the recovery of a person from injury through the immobilization or partial immobilization of an arm, wrist, and/or hand of said person. The splint may include dynamic traction elements and/or support inserts, which may be customizable to a desired configuration, to allow for individualized treatment for recovery from an injury.

18 Claims, 21 Drawing Sheets

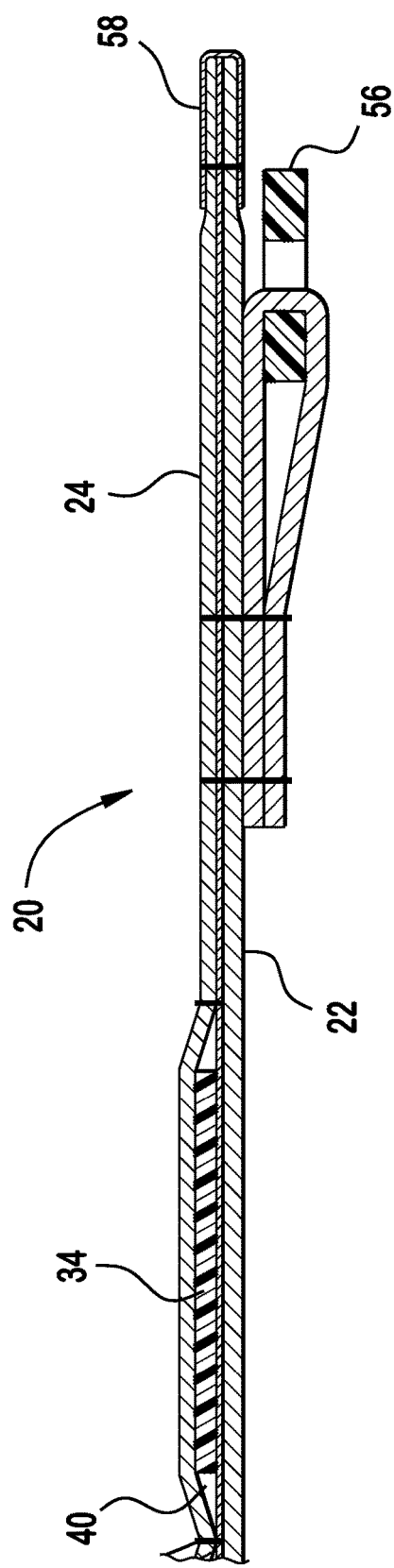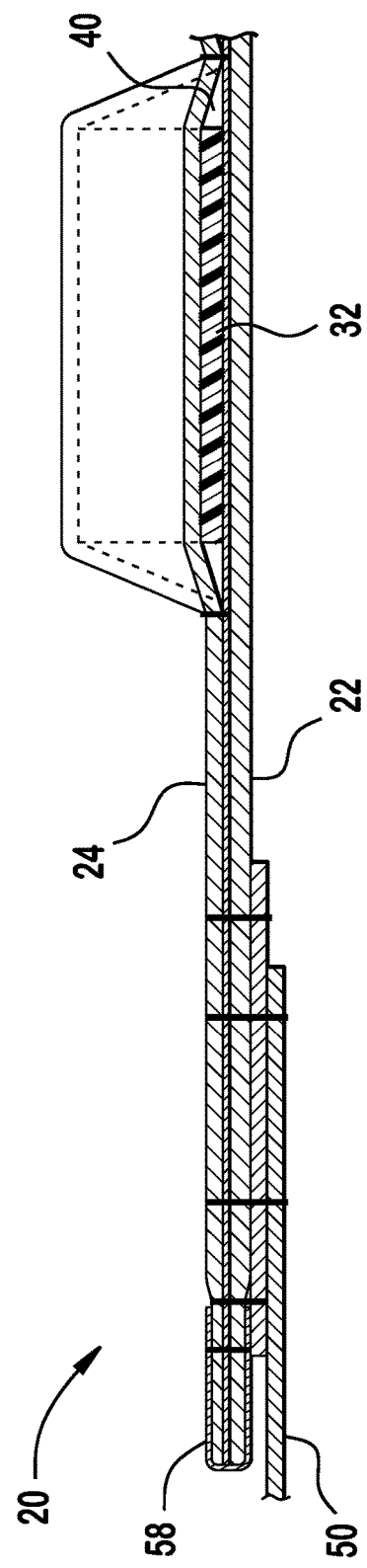

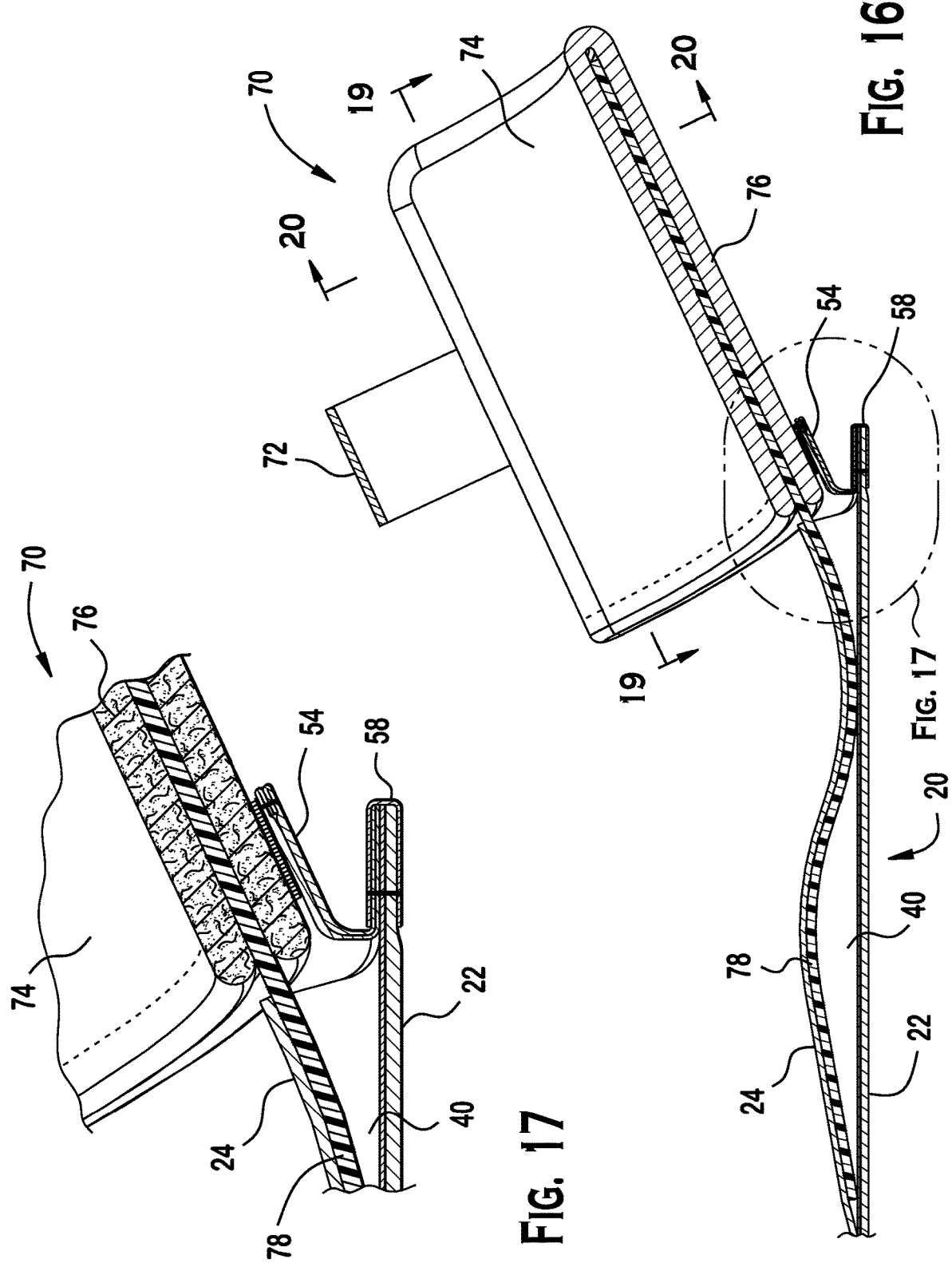

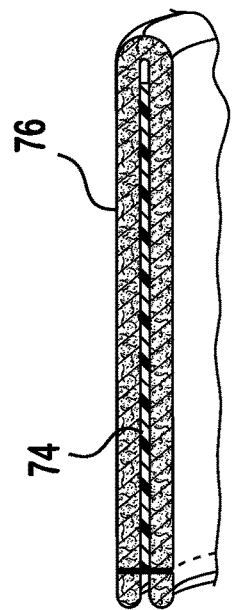
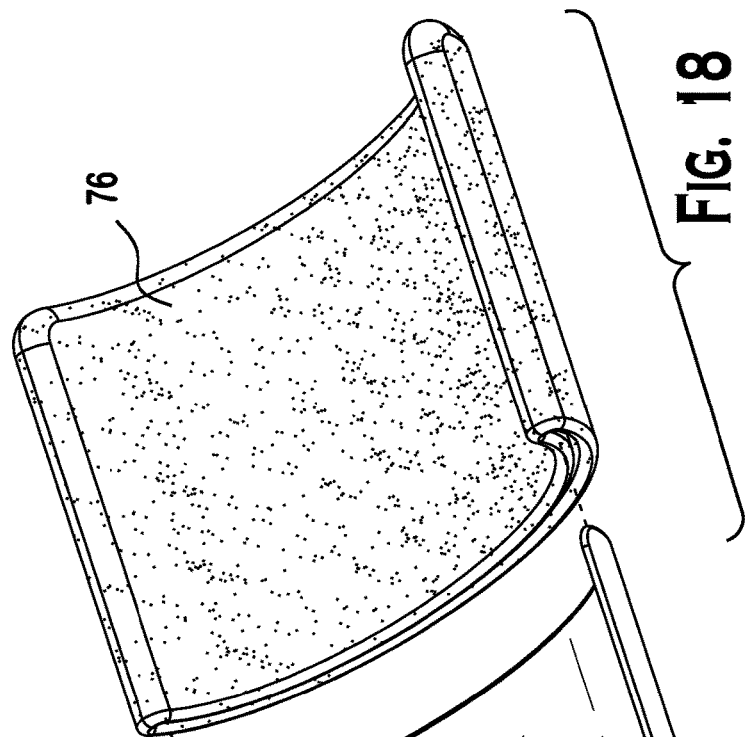
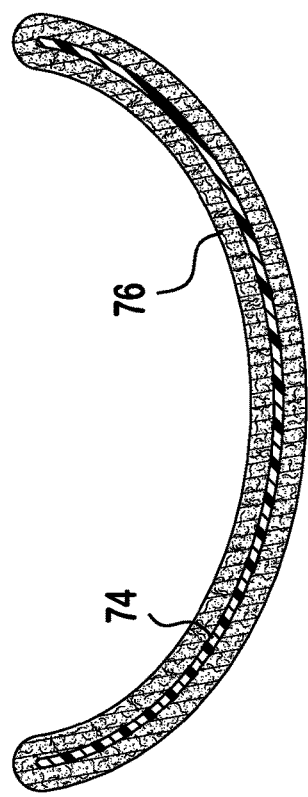
FIG. 19
FIG. 20
FIG. 18

SPLINT AND METHOD OF USE

CROSS REFERENCE TO RELATED APPLICATIONS

This application claims priority to the following US Patent Applications: (1) U.S. application Ser. No. 14/663,626, filed Mar. 20, 2015; and (2) U.S. Design patent application Ser. No. 29/580,387, filed Oct. 7, 2016; each of which is hereby incorporated by reference herein as if fully set forth in its entirety.

BACKGROUND

The present invention relates generally to devices used for the support and immobilization of limbs and, more specifically, to a splint for a portion of the arm, wrist, and hand of a person.

Splints are commonly used to immobilize and support a limb. In many cases, the splint may immobilize a broken bone or damaged joint, or provide support for a joint during physical activity. A splint traditionally provides a prefabricated bandage member configured to enclose and often encase a limb, or portion of limb, in order to provide the required support and immobilization required for effective treatment and healing of the limb.

It may be advantageous to provide a splint which is customizable to a user's specific shape and movements; may conform to a desired orientation or shape; may provide additional support outside the main body of the splint; may provide adjustable supports; may allow for quick and efficient use; can be easily manufactured; and/or is preferably efficient to manufacture.

SUMMARY

In one aspect, one preferred embodiment of the present invention is directed to a splint adapted for use on at least a portion of an arm of a person. The splint may comprise a main splint body configured to wrap around a portion of the arm such that the splint extends longitudinally over at least a portion of the forearm, over the wrist, and/or over the first portion of the hand of a person. The main body may further comprise a pocket located on a side of the main splint body. A support member may also be positioned into the pocket. The support member is preferably configured to provide a contoured configuration to the main splint body and to provide resistance against moving the arm in a manner to drive the main splint body out of the contoured configuration.

In another aspect, one embodiment of the present invention is directed to a splint adapted for use on at least a portion of an arm of a person. The splint may comprise a main splint body configured to wrap around a portion of the arm such that the splint extends longitudinally over at least a portion of the forearm, over the wrist, and/or over the first portion of the hand of a person. The main body may further comprise a pocket located on a side of the main splint body. A support member may also be positioned into the pocket. The support member is preferably configured to be heated such that after heating, the support member is placed on the person and can then be configured such that the customized contoured configuration is provided to the person.

In another aspect, one embodiment of the present invention is directed to a splint adapted for use on at least a portion of an arm of a person. The splint may comprise a main splint body configured to wrap around a portion of the arm such that the splint extends longitudinally over at least a portion of the forearm, over the wrist, and/or over the first portion of the hand of a person. The main body may further comprise a pocket located on a side of the main splint body. A support member may also be positioned into the pocket such that the support member is removeable from and insertable into the pocket.

In another aspect, one embodiment of the present invention is directed to a splint adapted for use on at least a portion of an arm of a person. The splint may comprise a support member which is formed by an elongated member that is generally aligned parallel to a longitudinal axis of the splint.

In another aspect, one embodiment of the present invention is directed to a splint adapted for use on at least a portion of an arm of a person. The splint may further comprise a second support member which is configured for insertion into the main splint body. The second support member may be configured to provide a contoured configuration to the main splint body and to provide resistance against moving the arm in a manner to drive the main splint body out of the contoured configuration.

In another aspect, one embodiment of the present invention is directed to a splint adapted for use on at least a portion of an arm of a person. The splint may provide the ability to exchange the second support member with the support member. In this way, the support member may be removed from the pocket and the second support member may be disposed within the pocket.

In another aspect, one embodiment of the present invention is directed to a splint adapted for use on at least a portion of an arm of a person. The main splint body may further comprise a bore configured to receive a portion of the hand of the person in order to facilitate alignment of the main splint body on the arm.

In another aspect, one embodiment of the present invention is directed to a splint adapted for use on at least a portion of an arm of a person. The main splint body may further comprises a plurality of supplemental pockets and supplemental support members. The supplemental support members may be configured to be insertable and removeable from the plurality of supplemental pockets.

In another aspect, one embodiment of the present invention is directed to a splint adapted for use on at least a portion of an arm of a person. The main splint body may further comprises a plurality of supplemental pockets and supplemental support members. The supplemental support members may be configured to be insertable and removeable from the plurality of supplemental pockets. The supplemental support members may be configured to be re-shaped and/or re-contoured after being heated.

In another aspect, one embodiment of the present invention is directed to a splint adapted for use on at least a portion of an arm of a person. The plurality of supplemental pockets and plurality of supplemental support members may further be longitudinally aligned with the pocket such that one of the plurality of support members can be longitudinally aligned with either the support member or the second support member when they are disposed within the main splint body.

In another aspect, one embodiment of the present invention is directed to a splint adapted for use on at least a portion of an arm of a person. The splint comprises a main splint body configured to be positioned around the portion of the arm such that the splint extends longitudinally over: at least a portion of a forearm, over a wrist, and over a first portion of a hand. The splint further comprises a dynamic traction attachment that is configured to detachably attach to the main splint body. The dynamic traction attachment comprises an arcuate extension. The arcuate extension is configured to extend past a longitudinal end of the main splint body to cover a portion of some fingers of the hand on which the main splint body extends over. At least one finger sling is attached to the dynamic traction attachment, wherein the arcuate extension is configured to locate the at least one finger sling adjacent to a finger of the hand on which the main splint body extends over such that the finger can be placed inside the at least one finger sling.

In another aspect, one embodiment of the present invention is directed to a splint adapted for use on at least a portion of an arm of a person. The splint may comprise a main splint body configured to be positioned around the portion of the arm such that the splint extends longitudinally over: at least a portion of a forearm, over a wrist, and over a first portion of a hand. The splint may further comprise a dynamic traction attachment that is configured to detachably attach to the main splint body. The dynamic traction attachment may comprise an arcuate extension. The arcuate extension may be configured to extend past a longitudinal end of the main splint body to cover a portion of some fingers of the hand on which the main splint body extends over. At least one finger sling may be attached to the dynamic traction attachment, wherein the arcuate extension can be configured to locate the at least one finger sling adjacent to a finger of the hand on which the main splint body extends over such that the finger can be placed inside the at least one finger sling. A portion of the dynamic traction attachment may have a shape and/or contour that is configured to be repeatedly adjusted so that the splint may be repeatedly re-shaped, re-contoured and/or re-customized.

In another aspect, one embodiment of the present invention is directed to a splint adapted for use on at least a portion of an arm of a person. The splint may comprise a main splint body configured to be positioned around the portion of the arm such that the splint extends longitudinally over: at least a portion of a forearm, over a wrist, and over a first portion of a hand. At least one finger sling may be attached to the main splint body, wherein the finger sling can be configured to be located adjacent to a finger of the hand on which the main splint body extends over such that the finger can be placed inside the at least one finger sling.

In another aspect, one embodiment of the present invention is directed to a splint adapted for use on at least a portion of an arm of a person. The splint may comprise a main splint body configured to be positioned around the portion of the arm such that the splint extends longitudinally over: at least a portion of a forearm, over a wrist, and over a first portion of a hand. The main splint body may comprise a pocket. At least one support insert may be configured to be removeably inserted into the pocket. The at least one support insert may have a contour that is configured to be adjusted at least one of immediately prior to being inserted into the at least one pocket and after being inserted into the at least one pocket such that the plurality of support inserts can be customized to the person.

In another aspect, one embodiment of the present invention is directed to a splint adapted for use on at least a portion of an arm of a person. The splint may comprise a main splint body configured to be positioned around the portion of the arm such that the splint extends longitudinally over: at least a portion of a forearm, over a wrist, and over a first portion of a hand. The main splint body may comprise a pocket. At least one support insert may be configured to be removeably inserted into the pocket. The at least one support insert may have a shape and/or contour that is configured to be repeatedly adjusted so that the splint may be repeatedly re-shaped, re-contoured and/or re-customized.

In another aspect, one embodiment of the present invention is directed to a splint adapted for use on at least a portion of an arm of a person. The splint may comprise a main splint body configured to be positioned around the portion of the arm such that the splint extends longitudinally over: at least a portion of a forearm, over a wrist, and over a first portion of a hand. The main splint body may comprise at least one pocket. A plurality of support inserts may be configured to be removeably inserted into the at least one pocket. The plurality of support inserts may have a contour that is configured to be adjusted at least one of immediately prior to being inserted into the at least one pocket and after being inserted into the at least one pocket such that the plurality of support inserts can be customized to the person.

In another aspect, one embodiment of the present invention is directed to a splint adapted for use on at least a portion of an arm of a person. The splint may comprise a hinge that may have first and second legs extending from a center portion thereof. The first leg may be configured to be positioned on a first splint portion that covers a portion of the forearm. The second leg may be configured to be positioned on a second splint portion that covers a portion of the hand. The center portion may be configured to be positioned on a third splint portion that covers the wrist. The hinge may be configured to lock the first leg at various angles with respect to the second leg thereby locking the hand at various angles with respect to the forearm.

In another aspect, one embodiment of the present invention is directed to a splint adapted for use on at least a portion of an arm of a person. The splint may comprise a hinge that is configured to lock the hand at various angles with respect to the forearm.

In another aspect, one embodiment of the present invention is directed to a splint adapted for use on at least a portion of an arm of a person. The splint may comprise heatable, moldable orthoplastic struts.

In another aspect, one embodiment of the present invention is directed to a splint adapted for use on at least a portion of an arm of a person. The splint may include heatable, moldable orthoplastic struts and an insert with an extension thereon. The splint, orthoplastic struts, and insert with an extension thereon may all be microwave heatable.

In another aspect, one embodiment of the present invention is directed to a splint adapted for use on at least a portion of an arm of a person. The splint may include an insert with an extension thereon. The insert with the extension thereon may be configured to support fingers of the arm the splint is positioned on.

In another aspect, one embodiment of the present invention is directed to a splint adapted for use on at least a portion of an arm of a person. The splint may include an insert with an extension thereon. The insert with the extension thereon may be configured to support fingers of the arm with semi-rigid immobilization.

In another aspect, one embodiment of the present invention is directed to a splint adapted for use on at least a portion of an arm of a person. The splint may include an insert with an extension thereon. The insert with the extension thereon may be configured to support fingers of the arm the splint is positioned on. The insert and/or extension may be moldable to allow various resting positions of the fingers.

In another aspect, one embodiment of the present invention is directed to a splint adapted for use on at least a portion of an arm of a person. The splint may be configured to allow protected partial motion of the digits as opposed to rigid immobilization.

In another aspect, one embodiment of the present invention is directed to a splint adapted for use on at least a portion of an arm of a person. The splint may include an insert with an extension thereon. The insert with the extension thereon may be configured to support the fingers and thumb of the arm the splint is positioned on.

In another aspect, one embodiment of the present invention is directed to a splint adapted for use on at least a portion of an arm of a person. The splint may include an insert with an extension thereon. The insert with the extension thereon may be configured to support the fingers and thumb of the arm with semi-rigid immobilization.

In another aspect, one embodiment of the present invention is directed to a splint adapted for use on at least a portion of an arm of a person. The splint may include an insert with an extension thereon. The insert with the extension thereon may be configured to support the fingers and the thumb of the arm the splint is positioned on. The insert and/or extension may be moldable, semi-flexible, and/or bendable to allow various resting positions of the fingers and thumb.

In another aspect, one embodiment of the present invention is directed to a splint adapted for use on at least a portion of an arm of a person. The splint may be configured to allow protected partial motion of the digits and thumb as opposed to rigid immobilization.

In another aspect, one embodiment of the present invention is directed toward a method of providing a splint adapted for use on at least a portion of an arm of a person. The method may further comprise providing a main splint body configured to wrap around a portion of the arm such that the splint extends longitudinally over at least a portion of a forearm, over a wrist, and/or over a first portion of a hand. The main body may further comprise a pocket. The method may also include providing a support member positioned in the pocket, the support member being configured to provide a contoured configuration to the main splint body and to provide resistance against moving the arm in a manner to drive the main splint body out of the contoured configuration.

In another aspect, one embodiment of the present invention is directed toward a method of providing a splint adapted for use on at least a portion of an arm of a person. The method may further comprise providing a main splint body configured to be positioned around a portion of the arm such that the splint extends longitudinally over at least a portion of a forearm, over a wrist, and/or over a portion of a hand. The main body may further comprise a pocket. The method may also include providing a plurality of support inserts configured to be removeably inserted into the at least one pocket. Each of the plurality of support inserts may have a contour that is configured to be adjusted at least one of immediately prior to being inserted into the at least one pocket and after being inserted into the at least one pocket such that the plurality of support inserts can be customized to the person.

In another aspect, one embodiment of the present invention is directed toward a method of providing a splint adapted for use on at least a portion of an arm of a person. The method may further comprise providing a main splint body configured to be positioned around a portion of the arm such that the splint extends longitudinally over at least a portion of a forearm, over a wrist, and/or over a portion of a hand. The method may also include providing a dynamic traction attachment that is configured to detachably attach to the main splint body. The insert may comprise at least one finger sling attached thereto. The dynamic traction attachment may be configured to locate the at least one finger sling adjacent to a finger of the hand on which the main splint body is positioned over such that the finger can be placed inside the at least one finger sling.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 7 is a cross-sectional view of the main splint body of FIG. 5 as taken along the line 7-7 in FIG. 5. The flat support member is shown inserted into a pocket in the main splint body. Additionally, a strap is shown disposed on the exterior of the main splint body.

FIG. 8 is a cross-sectional view of the main splint body of FIG. 5 as taken along the line 8-8 in FIG. 5. A tab is illustrated in an open position to allow for insertion of a support member into a pocket. The main splint body is preferably provided with a strap on the exterior surface.

FIG. 16 is a partial side view cross section of the second support member of FIG. 12 disposed within a pocket of the main splint body. The arcuate extension is preferably angled away from the main splint body after insertion. A sleeve is preferably provided to enclose the arcuate extension of the second support body. The sleeve may further support the adjustable band of the second support member.

FIG. 17 is an enlarged partial view of the cross section of FIG. 16. When the second support member is disposed within the pocket of the main splint body, a tab is oriented in the open position to allow the arcuate extension to extend outwards.

FIG. 18 is a perspective view of the second support member. Preferably, the sleeve is provided as a separate member from the arcuate extension and configured to slide onto the arcuate extension. The sleeve may be disposable or interchangeable depending on surface comfort. Additionally, ice packs or heating gel can be incorporated into the sleeve without departing from the scope of the present invention. Alternatively, a fluid treatment can be incorporated into the sleeve, such as a moisturizer, burn cream, anti-biotic cream, etc. without departing from the scope of the present invention. While a preferred configuration of the arcuate extension is shown Those of ordinary skill in the art will appreciate from this disclosure that any desired shape of the arcuate extension can be used without departing from the scope of the present invention. Furthermore, the arcuate extension can have holes therethrough to reduce weight. While the arcuate extension is shown being integral with the second support member, Those of ordinary skill in the art will appreciate from this disclosure that the arcuate extension may be detachably engaged with the second support member. This can allow the arcuate extension to be added to the splint without having to interchange any support members in the main body of the splint.

FIG. 19 is a cross sectional view of the arcuate extension of FIG. 16 as taken along the line 19-19 of FIG. 16. The sleeve is preferably disposed on the arcuate extension.

FIG. 20 is a cross sectional view of the arcuate extension of FIG. 16 as taken along the line 20-20 of FIG. 16. The arcuate extension is provided with the sleeve in position thereover.

DETAILED DESCRIPTION OF THE PREFERRED EMBODIMENTS

Figure 1:
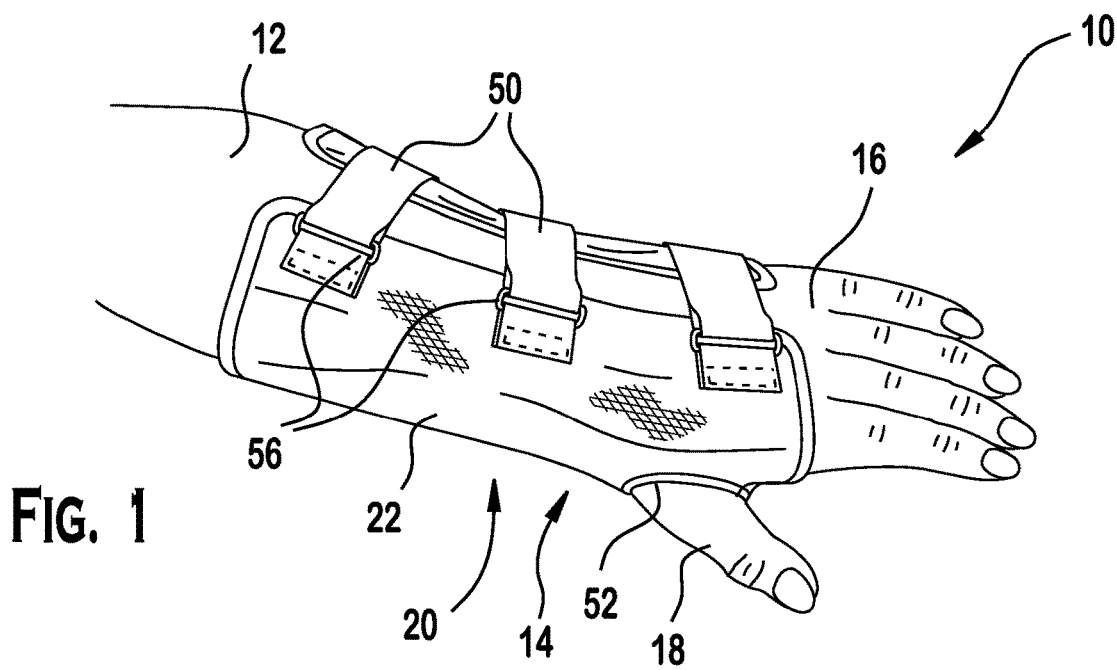
FIG. 1 is a perspective view of a preferred embodiment of the splint according to the present invention. The splint may be positioned in place on a portion of person's forearm, wrist, and hand. Additionally, the splint is shown only partially enclosing the circumference of the arm, wrist, and forearm. Those of ordinary skill in the art will appreciate from this disclosure, however, that the splint may fully enclose the circumference of the arm during use, or only partially enclose the circumference without departing from the scope of the invention. Additionally, it shows that the splint may support a portion of the forearm, wrist, and hand, however, the splint may support any one of the above, or all of them, without departing from the scope of the invention.

Certain terminology is used in the following description for convenience only and is not limiting. The words "right", "left", "top", "bottom", designate directions in the drawings to which reference is made. The term "splint", as used in the claims and associated portions of the specification, is defined as meaning "any medical device used for the support and/or immobilization of limbs or appendages". "Vertical" refers to a generally up and down position, while "horizontal" refers to a generally left to right position. The term "longitudinal axis" is used throughout the claims and disclosure in reference to both the splint and the arm of a person. It should be understood that a longitudinal axis of the arm should generally refer to the length of the arm from the elbow to fingers as a general reference for positioning the splint. The term "interior", as used in the claims and corresponding portions of the specification means the side of the invention configured to contact the person. The term "exterior" similarly defines the surface generally oriented away from the person. The term "bore" refers to generally a through-hole within the main splint body. Additionally, the words "a" and "one" are defined as including one or more of the referenced items unless specifically stated otherwise. The terminology includes the words above specifically mentioned, derivatives thereof, and words of similar import.

Referring to FIGS. 1-30, wherein like numerals indicate like elements throughout, preferred embodiments of a splint according to the present invention are shown and generally designated as 10. Briefly speaking the splint 10 can be worn around an arm, a wrist, hand, and/or other limb of a person who is looking to provide additional support and/or immobilization to support health and recovery. The splint may fully or partially enclose the circumference of the arm, wrist, and/or hand without departing from the scope of the invention.

Referring now to FIG. 1, the splint 10 is preferably formed from a flexible, synthetic material such that the splint is configured to contour to the user's shape, however those of ordinary skill in the art will appreciate from this disclosure that any material, such as a cloth or bandage wrap may be used without departing from the scope of the invention. The splint is illustrated as enclosing the arm 12, wrist 14, and the hand 16 of a person, however, the splint may extend across any range of the person.

Figure 2:
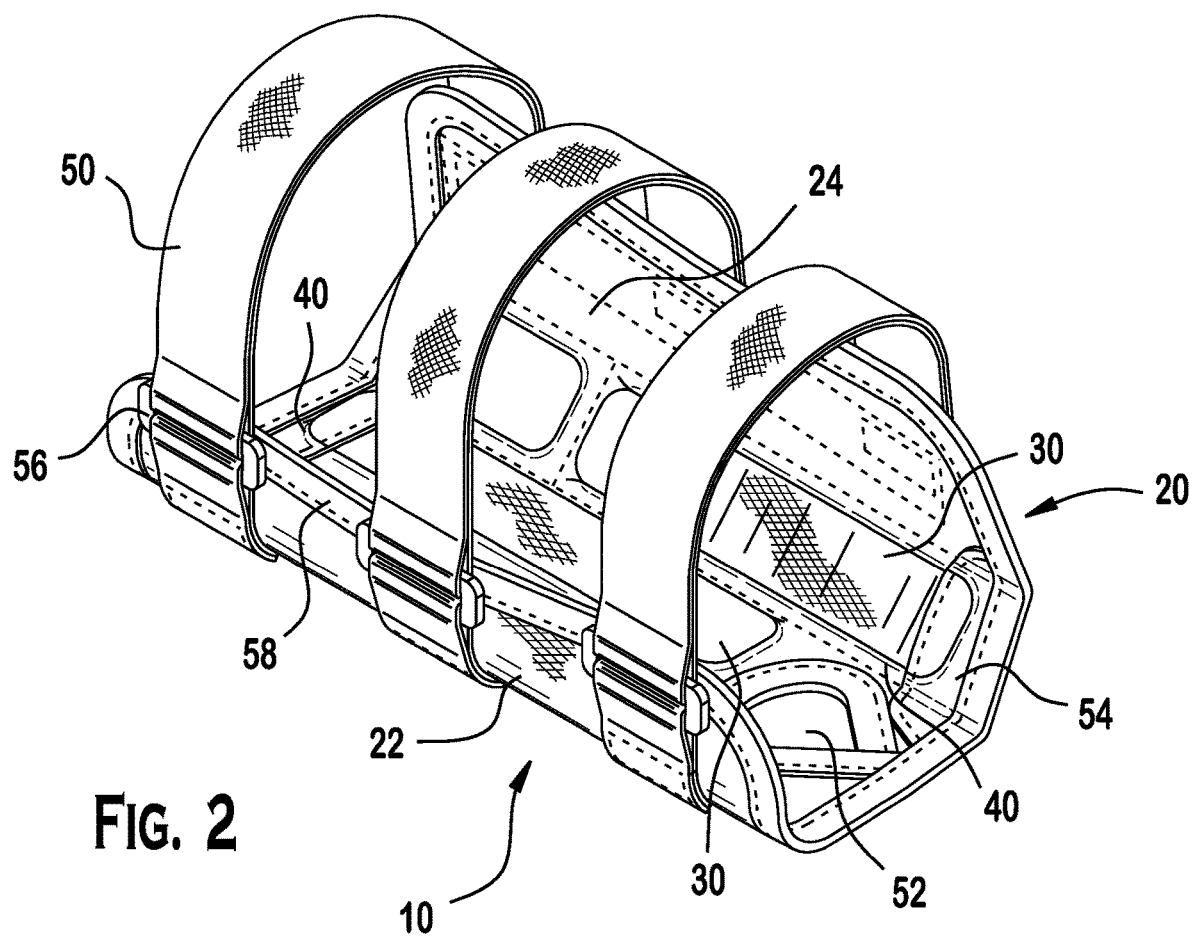
FIG. 2 is another perspective view of the splint of FIG. 1, without being placed in position on a person. The splint is preferably secured with three straps as illustrated, however, any number of straps may be used. Additionally, those of ordinary skill in the art will appreciate from this disclosure that any means of securement of the splint may be used without departing from the scope of the present invention. Several support members are illustrated in cut-away views disposed within pockets in the main body of the splint. The support members and pockets are preferably disposed longitudinally along the main splint body and aligned parallel with one another, however, those of ordinary skill in the art will appreciate from this disclosure that the support members may be configured in any orientation without departing from the scope of the present invention.

Referring to FIG. 2, a first preferred embodiment of the splint of the present invention is shown. The splint 10 may include a main body 20 which generally encloses the arm. The main body 20 may be formed of multiple layers. For example, the outer shell may be formed of neoprene, wherein an inner lining may be made of cotton and/or various thicknesses of padding. However, those of ordinary skill in the art will recognize from this disclosure that the main body may be formed of any number of layers, including a single layer, and any suitable material without departing from the scope of the invention. The main body 20 can include a series of straps 50 which connect with buckles 56 to secure the main body onto the arm of the user. In a preferred embodiment, there are shown three straps 50, however, any number of straps or other securing means may be used to secure the splint 10. Additionally, the splint can be secured around a person's arm using snaps, hook and loop material, adhesive, etc. without departing from the scope of the present invention. The straps 50 are preferably attached on the exterior surface 22 of the main body 20. Pockets 40 are preferably disposed on the interior surface 24 of the main body 20. Support members 30 are additionally provided and configured to be removeable and insertable into the pockets 40. The support members 40 preferably have two major surfaces and when viewed from above have a generally rectilinear shape with rounded edges. Preferably, the shape of the pockets 40 corresponds to the support members 30, however, those of ordinary skill in the art will appreciate from this disclosure that a single pocket 40 may contain several support members 30 without departing from the scope of the present invention. The support members may have holes therethrough to lighten weight while still providing the necessary contouring and resistance to movement out of a contoured configuration to the sling.

Advantageously, the main body 20 may further comprise a bore 52 disposed as a through-hole between the exterior surface 22 and the interior surface 24 of the main body 20. The bore 52 is preferably tear-drop shaped, however, any shape may be used. A thumb 18 of the user is preferably positioned through the bore 50, such that the splint 10 individually encloses the hand 16 and a thumb 18 separately in order to provide a more customized and secure fit. As such, the bore 52 is preferably positioned on the main body 20 in such a location as to line-up with the thumb 18 when the splint 10 is in position, however, those of ordinary skill in the art will appreciate from this disclosure that the bore may be positioned anywhere along the main body 20 or omitted altogether without departing from the scope of the present invention. The interior surface 24 of the main body 20 is oriented such that is contacts the skin of the user and similarly wraps around the contours of the arm 12, wrist 14, and hand 16.

Figure 3:
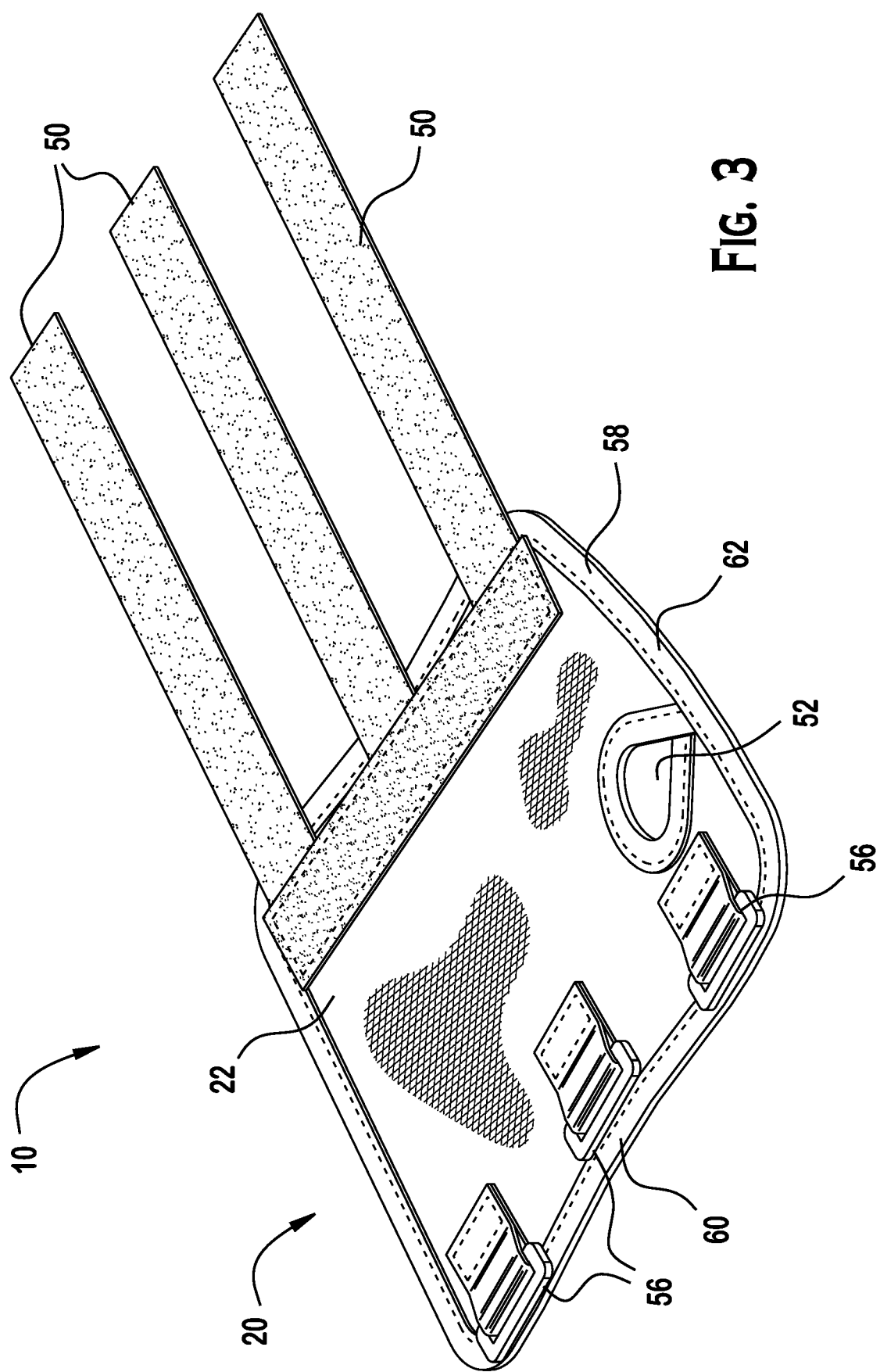
FIG. 3 is another perspective view of the exterior of main splint body of FIG. 1. The main splint body preferably attaches the straps to a lateral side of the exterior of the main splint body. A series of buckles are preferably attached on an opposing lateral side, such that when the splint is positioned in place, the straps may wrap around the users arm and wrist in order to secure to the opposing buckles. The strap and buckles may be disposed along any portion of the main splint body without departing from the scope of the present invention. Additionally, a bore is configured in the main splint body to preferably secure the thumb of the user, however, those of ordinary skill in the art will appreciate from this disclosure that the bore may be completely removed from the present invention or positioned for use with another finger without departing from the scope of the present invention.

Referring now to FIG. 3, an exterior surface 22 of the main body 20 of the splint 10 is shown. The exterior surface 22 preferably provides the attachment portions of the straps 50 and buckles 56. As illustrated, there are preferably three straps 50 and three corresponding buckles 56 positioned on opposing ends of the main body 20, however, any number of straps and buckles may be used. The bore 52 is illustrated as a through-hole in the main body 10, preferably positioned along a convex portion 62 of the main body 10 so as to facilitate insertion of the thumb 18 therethrough. The main body preferably has opposing lateral concave portions 60 and opposing lateral convex portions 62. In this way, the main body 20 preferably forms a generally rectilinear shape, however, those of ordinary skill in the art will appreciate form this disclosure that any shape may be used without departing from the scope of the present invention.

Figure 4:
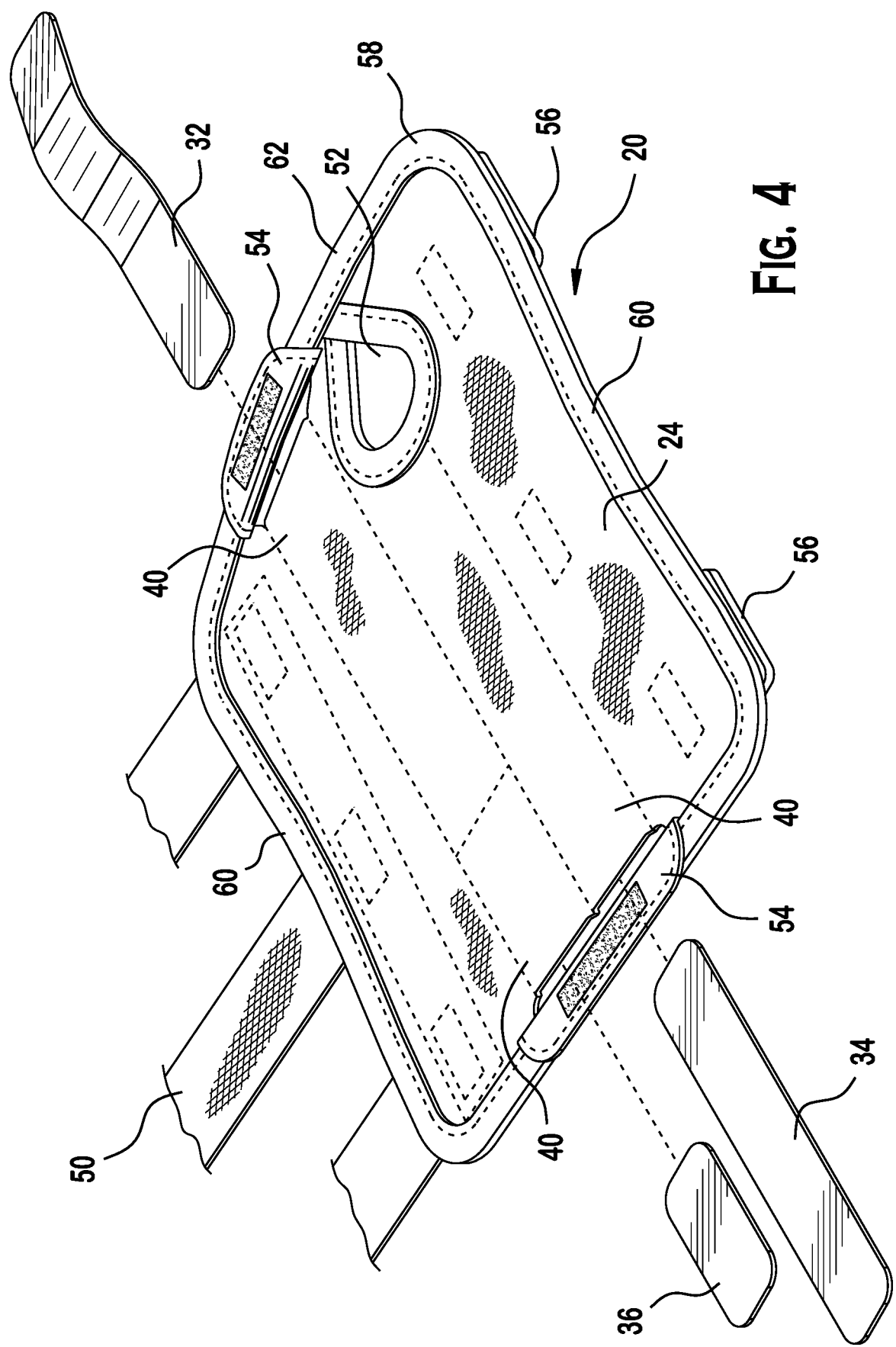
FIG. 4 is a perspective view of the interior of the main splint body of FIG. 1. Preferably, a number of support members are provided and configured to be insertable and removable from a plurality of pockets along the interior surface of the main splint body, however, those of ordinary skill in the art will appreciate from this disclosure that any number of support members and pockets may be used without departing from the scope of the present invention. Preferably, an angled support member, a flat support member, and a shortened support member are provided for insertion into pockets of corresponding size along the interior of the main splint body. Alternatively, the pockets may be disposed on the exterior of the main splint body without departing from the scope of the present invention.
Figure 5:
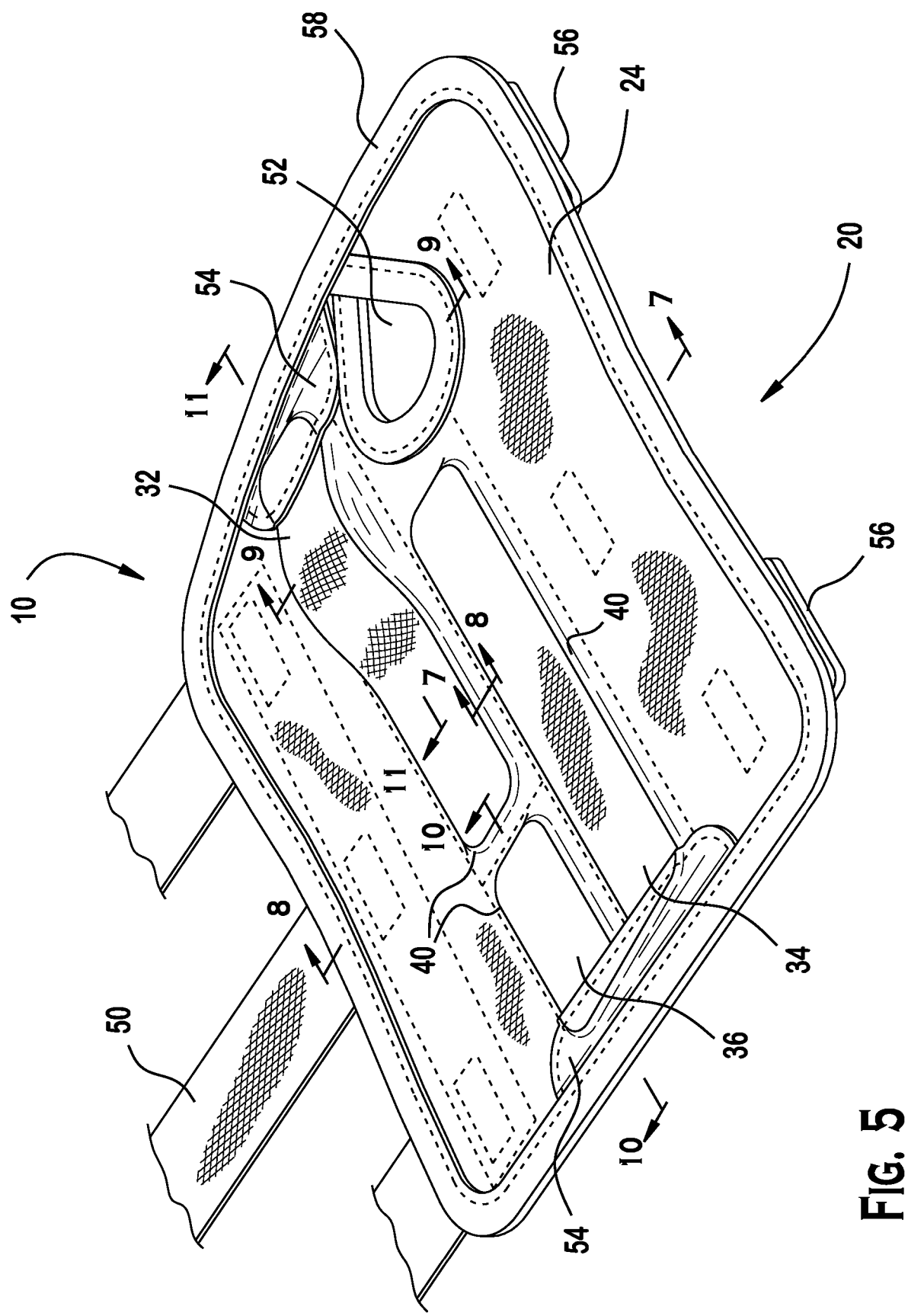
FIG. 5 is another perspective view of the interior of the main splint body of FIG. 1. The main splint body is shown with the support members in place within the pockets. While the support members are visible in the perspective view of the interior of the main splint body, in use, the support members are preferably concealed in the pockets of the main splint body. Preferably, the interior surface of the main splint body is configured of a flexible cloth material such that the material conforms to the contours of the support members, however, those of ordinary skill in the art will appreciate from this disclosure that any flexible material may be used without departing from the scope of the present invention. A series of tabs aligned with the pockets are provided to secure the support members within the pockets. A single tab me provided for multiple pockets or each pocket may be provided with an individual tab to secure the support members.
Figure 6:
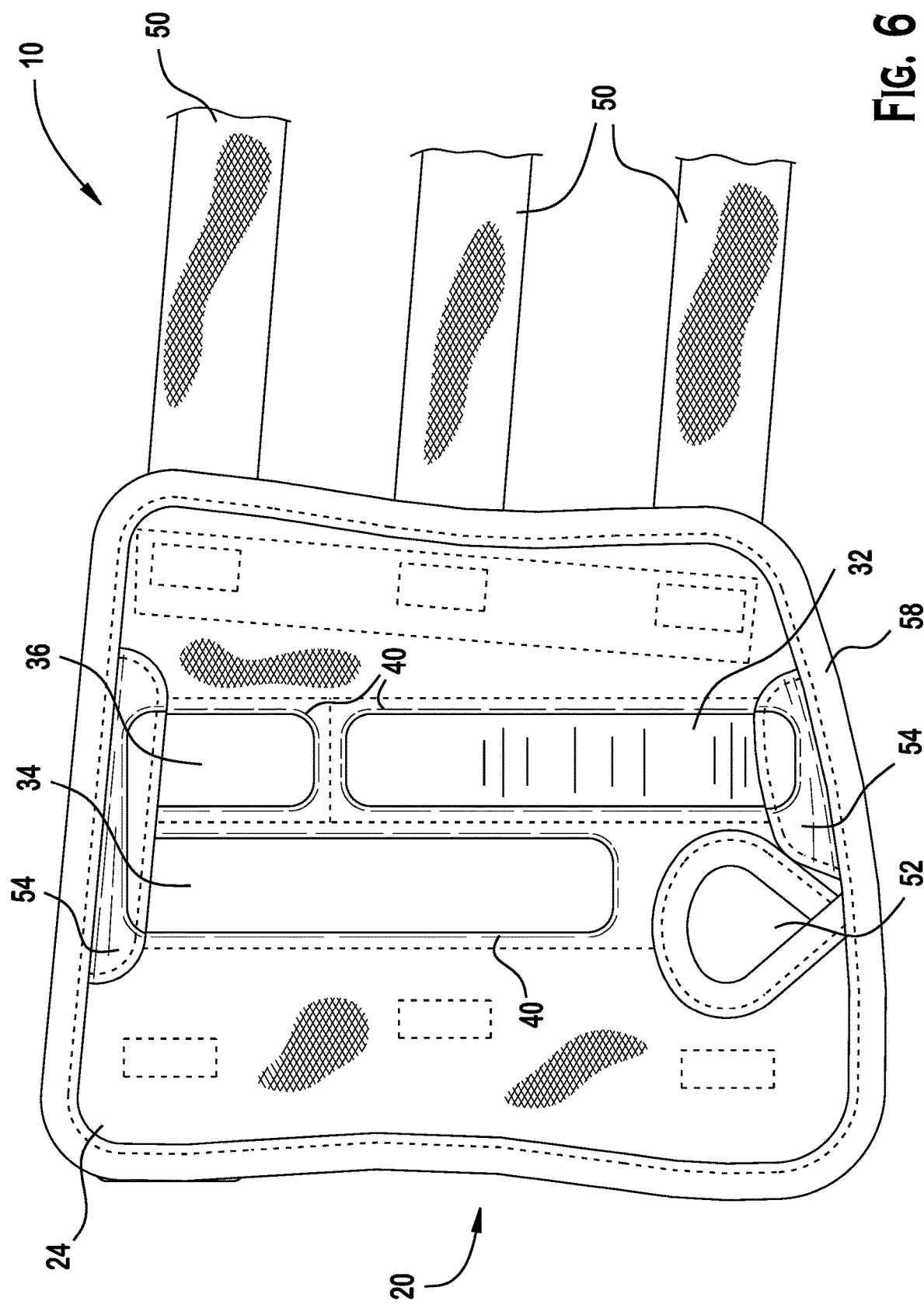
FIG. 6 is a top plan view of the interior of the main splint body of FIG. 1. A lining is preferably disposed about the perimeter of the main splint body as well as the bore provided for the thumb of the person. Those of ordinary skill in the art will appreciate from this disclosure that the lining may be completely removed from the present invention without departing from the scope of the present invention. As such, the entire main body can be formed of a single layer of material without departing from the scope of the present invention. A preferred embodiment of the present invention illustrates the flat and shortened support members enclosed with a single tab, while the angled support member is enclosed with a separate support member. Additionally, the support members are preferably inserted from opposing sides of the interior surface of the main splint body, however, those of ordinary skill in the art will appreciate from this disclosure that the support member may be inserted from any side of the main splint body without departing from the scope of the present invention. Alternatively, the support members may be attached to the main splint body with any suitable means of attachment, including hook and loop material, magnets, snaps, buttons, etc.
Figure 9:
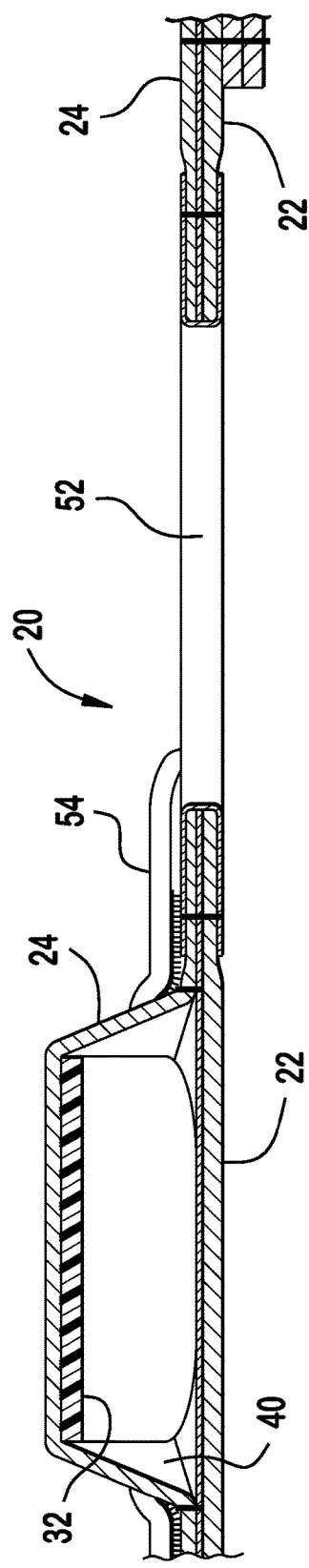
FIG. 9 is a cross-sectional view of the main splint body of FIG. 5 as taken along the line 9-9 in FIG. 5. The figure illustrates the angled support member disposed within a pocket and enclosed by a corresponding tab.
Figure 10:
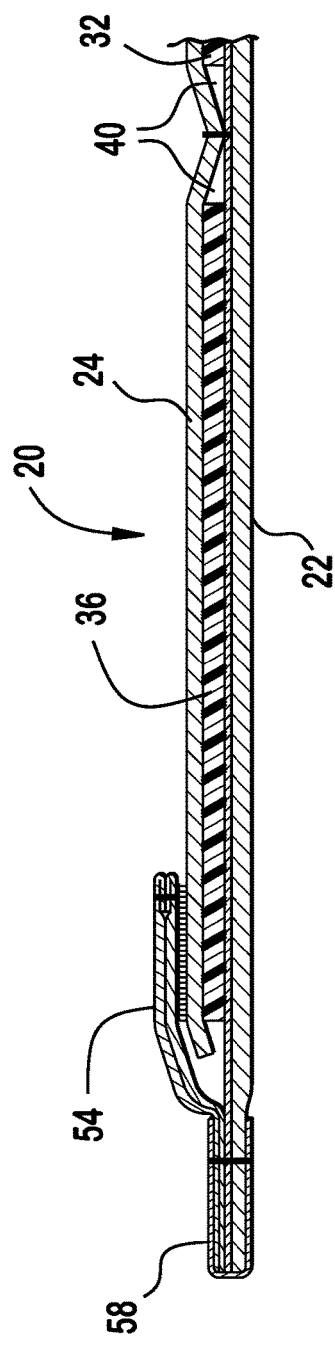
FIG. 10 is a cross-sectional view of the main splint body of FIG. 5 as taken along the line 10-10 in FIG. 5. The figure illustrates the shortened support body disposed within a pocket of the main splint body.

Referring now to FIGS. 4-6, an interior surface 24 of the main body 20 is illustrated. The interior surface 24 may further comprise pockets 40. The pockets 40 are configured so as to provide a free end along the convex portions 62 of the main body 20 configured to provide an opening. As such, support members 30 may be inserted into the pockets 40. The support members 30, as illustrated in FIG. 4, may include an angled support member 32, flat support member 34, and a shortened support member 36. The support members 30 are configured to provide a customized contour of the interior surface 24 of the main body 20 specific to the user of the splint. The support members may further be configured to be heat-formed such that upon heating, the support members may be adjusted and contoured to the specific shape of the arm 12, wrist 14, and hand 16 of the user. Preferably, the user may insert the support members 30 into pockets 40, heat the splint and support members, and then place the splint in position so that the support members form and cool to the shape of the user. However, those of ordinary skill in the art will appreciate from this disclosure that the support members 30 may be heated and re-shaped immediately prior to being inserted into the pockets 40, wherein "immediately prior" as used in this sentence is defined as within thirty minutes such that the support members 30 may be heated and re-shaped during the appointment time of a user such that at the end of the appointment the user may have a splint with custom-shaped support inserts. More preferably, "immediately prior" means that the support members 30 may be heated and re-shaped within fifteen minutes. More preferably, "immediately prior" means that the hinge 110 may be heated and re-shaped within ten minutes. More preferably, "immediately prior" means that the hinge 110 may be heated and re-shaped within five minutes. More preferably, "immediately prior" means that the hinge 110 may be heated and re-shaped within two minutes.

The support members 30 may be formed out of a thermoplastic material that becomes soft when heated and hard when cooled, therefore a user may easily adjust the shape and/or contour whenever needed. However, those of ordinary skill in the art will appreciate from this disclosure that the support members 30 may be formed out of any material whose shape and/or contour may be adjusted. Preferably, the support members 30 can be heated using common appliances, such as a microwave, stove, oven, or dryer, so that the support members 30 can be heated and re-shaped quickly in any location having a common appliance. The pockets 40 of the splint 10 may be lined with an insulating material so that a user is not burned while positioning the splint 10 with heated support members 30 on their arm, wrist, and/or hand. As such, the support members 30 can be conveniently and quickly reshaped and/or resized to best support the injury of a user as well as the contour of the user's arm and hand. The support members 30 can preferably be re-shaped and/or re-contoured repeatedly so that the support members 30 can be adjusted to the patient and condition being treated through specific molding and utilization of the pieces with progressive modifications throughout the healing and treat. process. The support members 30 are preferably configured to be repeatedly re-shaped and/or re-contoured without the use of any tools except a heating source.

The support members 30 are preferably formed by an elongated member that generally aligned parallel to a longitudinal axis of the splint. The axis is generally aligned with a longitudinal axis of the arm 12 of the user. The pockets 40 preferably have a shape which generally corresponds to shape of the support members 30, however, those of ordinary skill in the art will appreciate from this disclosure that any size and shape pocket and support member may be used without departing from the scope of the present invention.

Referring more specifically to FIG. 5, the support members 30 may be inserted into the pockets 40 and are preferably fully enclosed therein. Tabs 54 may be provided along the lining 58 of the main body 20 to enclose the openings of the pockets 40 and to retain the support members 30 inside of the pockets. Those of ordinary skill in the art will appreciate from this disclosure that the support members may be attached to the main body through any suitable attachment means, including Velcro, snaps, or buttons without departing from the scope of the present invention. Preferably, the angled support member 32 is disposed adjacent to a convex portion 62 of the main body and adjacent to the bore 52. The shortened support member 36 is preferably longitudinally aligned with the angled support member 32 along an opposing end of the main body 20. The flat support member 34 is preferably adjacent to the shortened support member 36, however, those of ordinary skill in the art will appreciate from this disclosure that the support members may be positioned anywhere along the main body without departing from the scope of the present invention. As illustrated, multiple different adjustable and/or moldable support members 30 are used to allow many variations of support to fit the exact nature of injury. The support members 30 may be located and shaped to align with the proper nerve, tendon and/or bony structures for protection and comfort.

Figure 11:
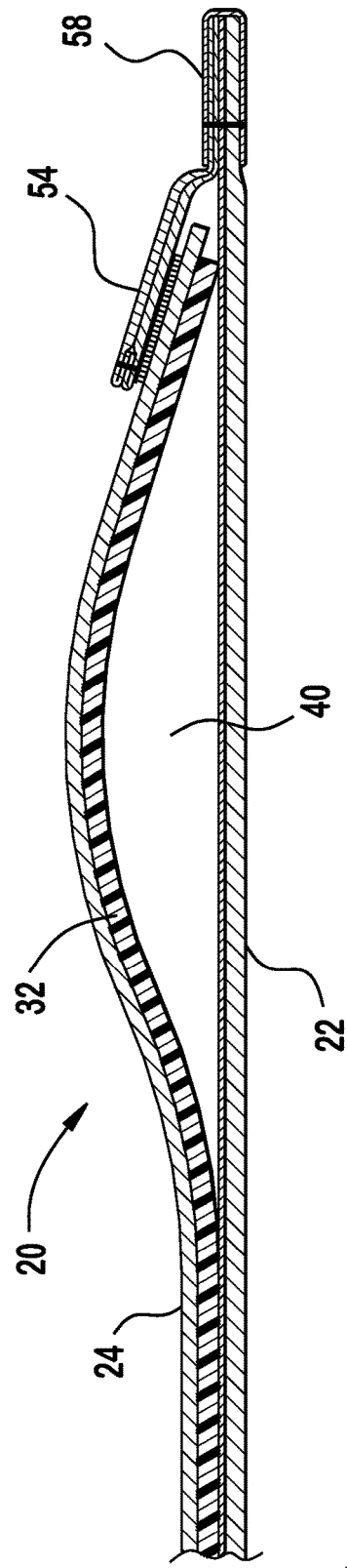
FIG. 11 is a cross-sectional view of the main splint body of FIG. 5 as taken along the line 11-11 in FIG. 5. The figure illustrates a portion of the angled support member is position within a pocket of the main splint body and enclosed by a tab.
Figure 12:
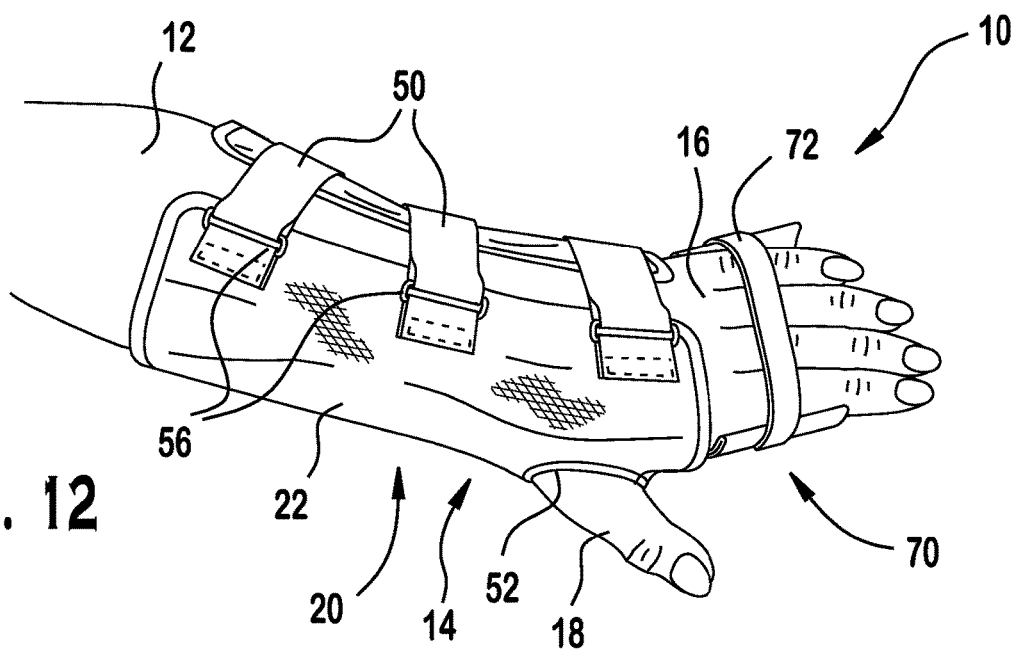
FIG. 12 is a perspective view of a second preferred embodiment of the splint of the present invention. A second support member is preferably provided to support and limit the movement of the fingers of the hand of the person. Those of ordinary skill in the art will appreciate from this disclosure that a second support member may provide support to any number of fingers or limbs without departing from the scope of the invention. The second support member is preferably disposed within a pocket of the main splint body and configured to extend outside of the pocket. The second support member may be configured to provide support to an individual finger or all fingers and may be used during sleep to provide additional support at night.
Figure 13:
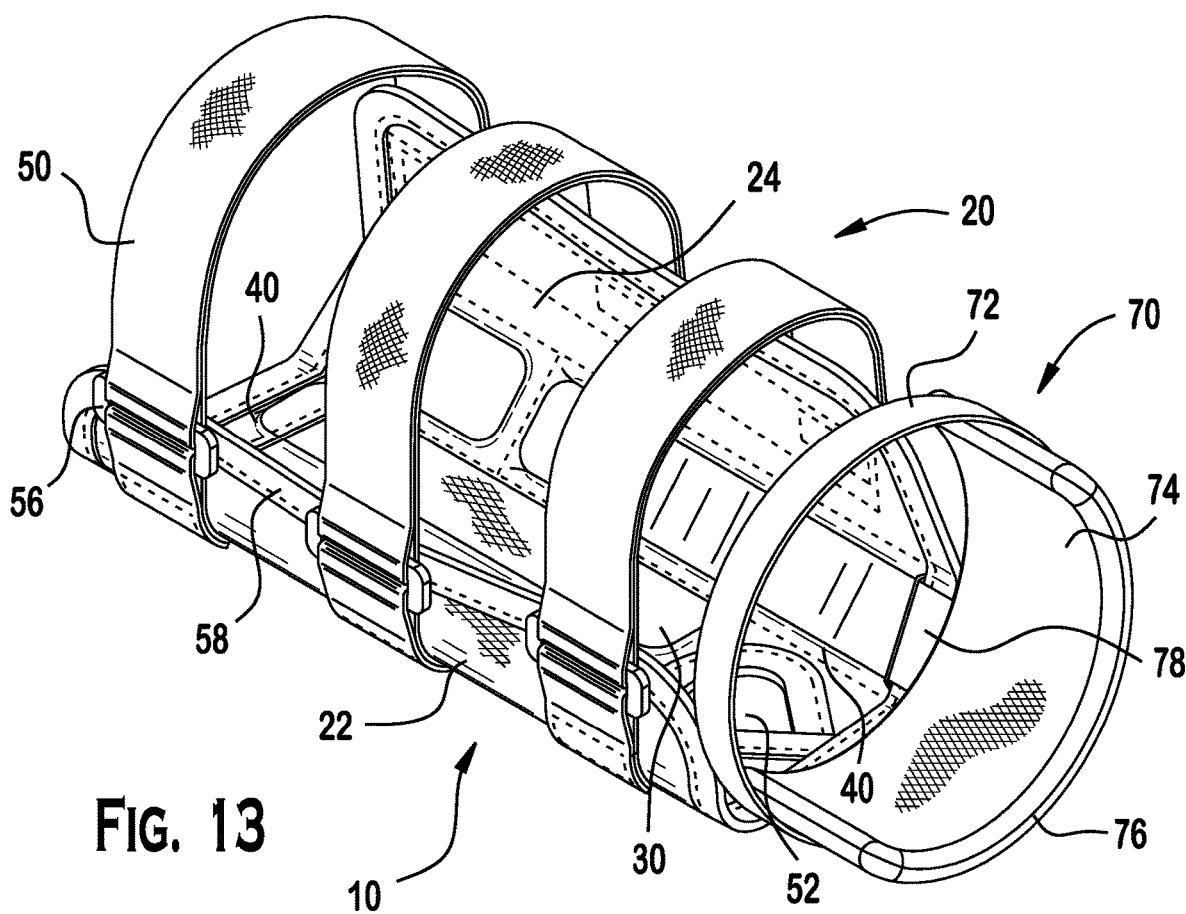
FIG. 13 is another perspective view of the main splint body of FIG. 12 with the second support member. The second support member preferably provides an arcuate extension on one end and an opposing end configured for insertion into the pocket of the main splint body. Those of ordinary skill in the art will appreciate from this disclosure that the second support member may be provided with any shape or contour without departing from the scope of the present invention. Preferably, the second support member has an adjustable band configured to enclose the fingers and secure them in position within the second support member.

Referring now to FIGS. 7-11, several section views of the splint according to FIG. 5 are shown. The interior surface 24 of the main body 20 preferably contours to the shape of the support members 30, whereas the outer surface of the main body can provide a smooth consistent contour around the circumference of the arm 12. It should be noted that the support members 30 may alternately be disposed along the exterior surface 22 of the main body without departing from the scope of the invention. Tabs 54 are further provided along the linin 58 of the interior surface 24 to enclose the openings of the pockets 40 once the support members are inserted into position. The tabs 54 may be of the same material as the main body 20 or of a separate rigid material. The tabs furthermore are preferably configured with a Velcro attachment to secure them to the interior surface 24, however, those of ordinary skill in the art will appreciate from this disclosure than any suitable attachment means may be used, such as a magnet, button, or zipper, without departing from the scope of the invention. With the support members 30 disposed within the pockets 40, the tabs 54 may be pressed onto the interior surface 24 against the support members to fully enclose them within the pockets. Referring specifically to FIG. 11, it should be noted that the interior surface 24 of the main body 20 contours to the shape of the angled support member 32, providing the customized contour configuration of the user's arm 12, wrist 14, and hand 16.

Figure 14:
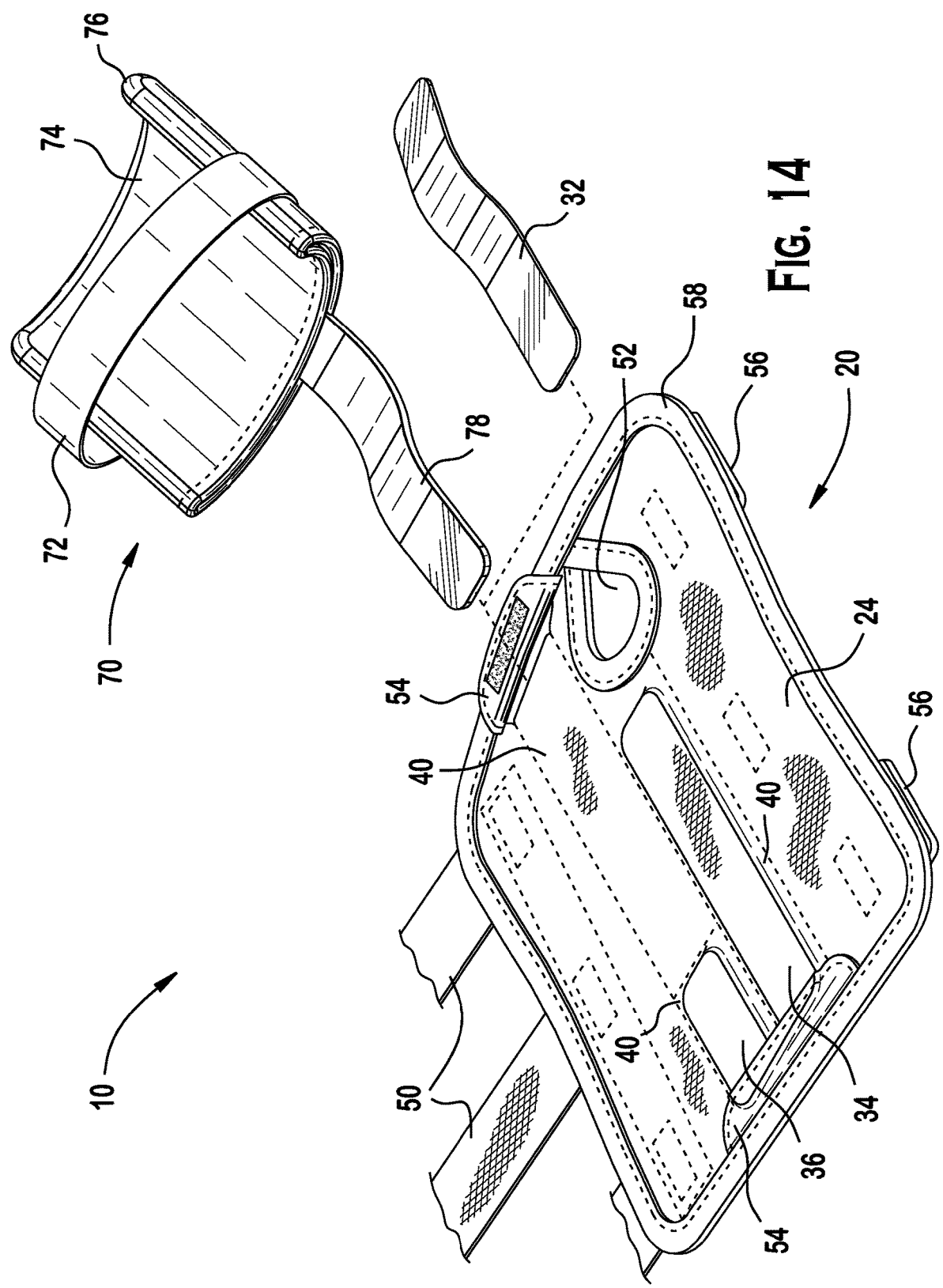
FIG. 14 is another perspective view of the main splint body of FIG. 12 with the second support member removed from the pocket. Preferably, the second support member is used in place of the angled support member, however, those of ordinary skill in the art will appreciate from this disclosure that any support member may be exchanged to use the second support member without departing from the scope of the present invention. Additionally, the second support member may be provided for use in addition to all the support members without the need for exchange.
Figure 15:
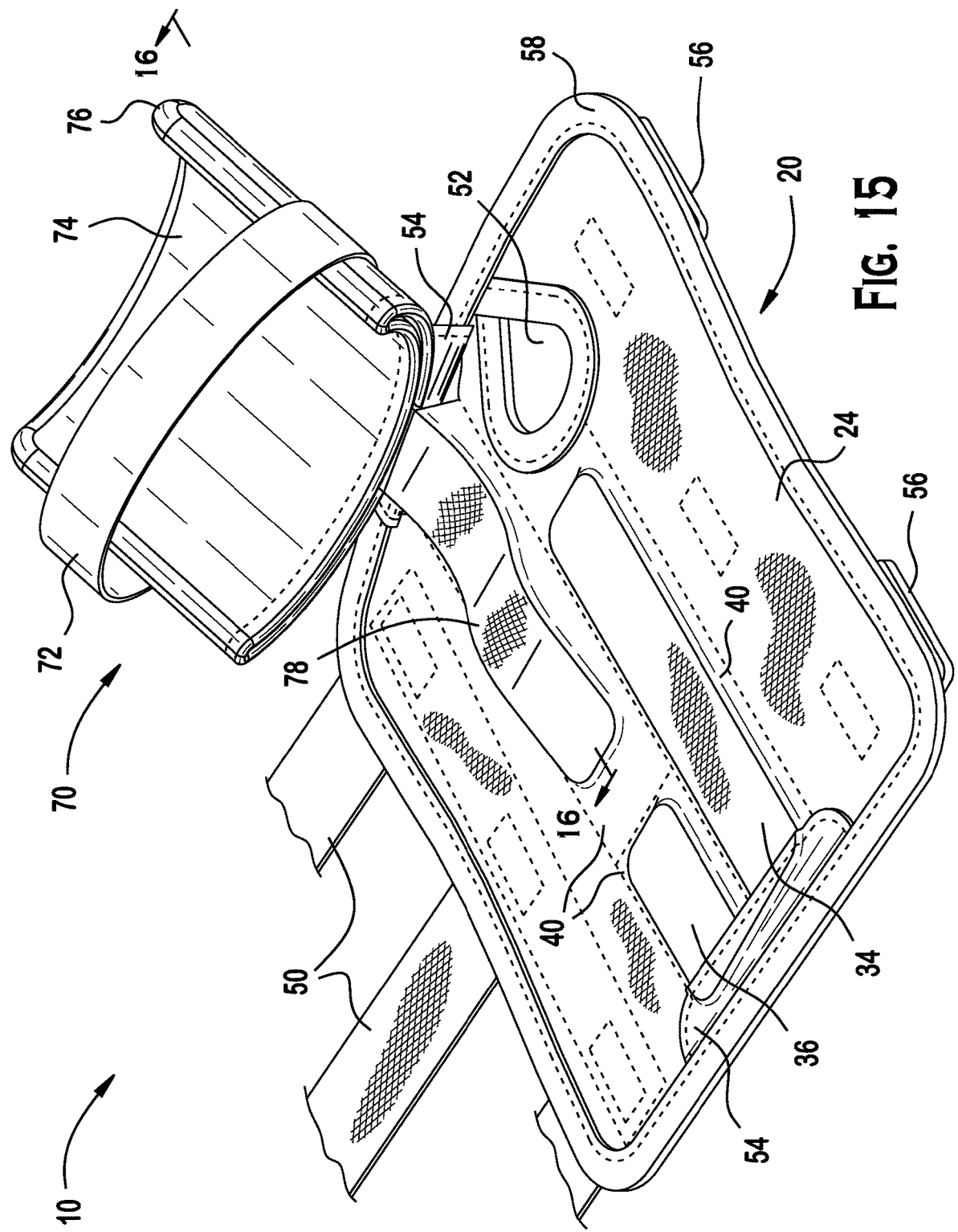
FIG. 15 is perspective view of the main splint body of FIG. 12 with the second support member inserted into a pocket of the main splint body. The second support member is preferably inserted into the pocket with the concave portion of the arcuate extension oriented toward the user's hand, however, the second support member may be oriented in any position without departing from the scope of the present invention.

Referring now to FIGS. 12-18, a second support member 70 may be provided as a separate attachment to the main body 20. The second support member 70 preferably provides an arcuate extension 74 and sleeve 76 which are configured to extend outside of the main body 20. An adjustable band 72 may also be provided to secure the arcuate extension 74 to the hand 16 of the user. The adjustable band 72 is preferably attached to the sleeve 76 with Velcro, however, any suitable connections means, such as a button or clip may be used without departing from the scope of the present invention. A second support insert 78 may be further provided to insert into a pocket 40 to secure and position the second support member 70. The second support member may be configured to provide support and recovery from finger pain or "trigger finger" and is preferably used at night to provide support to the hand 16 during sleep. The second support member 70 is preferably exchangeable with the angled support member 32, however, those of ordinary skill in the art will appreciate from this disclosure that the second support member may be positioned anywhere and be exchanged or added to any support member of pocket of the splint without departing from the scope of the present invention. The second support member 70 preferably inserts into the pocket 40 until the arcuate extensions 74 comes into contact with the lining 58 of the main body 20. As such, the second support member 70 may be used in place of the angled support member 32, as illustrated in FIG. 14, depending upon the type and location of support desired by the user. The second support insert 78 preferably shares a similarly contoured shape as the angled support member 32, and also, is similarly dimensioned to fill the corresponding pocket 40, however, those of ordinary skill in the art will appreciate from this disclosure that the second support insert 78 may be of any shape or dimension and attach to the main body by any suitable means, as previously discussed in relation to the support members 30.

Referring more specifically to FIGS. 18-20, a preferred embodiment of the second support member 70 is shown. The second support member 70 preferably has a removeable sleeve 76 which is positioned over the arcuate extension 74. As illustrated, the second support member 70, including the arcuate extension 74 and the second support insert 78 are preferably made of the same material as the support members 30 and continuous throughout, however, those of ordinary skill in the art will appreciate from this disclosure that the second support member made be made of separate material or comprise separate parts without departing from the scope of the present invention. Similar to the support members 30, the second support member 70 is preferably heat-formable and customizable to the hand 16 of the user. Advantageously, the second support member 70 may therefore provide a customized fit and support to the user's hand 16 and fingers. The sleeve 76 is preferably a flexible material to follow the contours of the arcuate extension 74, and removeable to allow for cleaning and repositioning.

It should be noted that those of ordinary skill in the art will appreciate from this disclosure that the present invention may further be used in accordance with any medical device used for the support and/or immobilization of any limb (including the foot, leg, neck, etc.) without departing from the scope of the invention.

Referring to FIGS. 1-20, one preferred embodiment of the present invention operates as follows. A user places the appropriate support members 30, for example heatable moldable orthopedic struts, and/or second support member 70 in position within the pockets. The user then heats the splint 10 and support members 30, 70 to induce a suitable heat-forming temperature. Once the supports are heat-formable, the user may then place the splint around the arm 12, wrist 14, and hand 16, preferably with the thumb disposed through the bore 52, and secure the splint 10 with the straps 50. Once in place, the support members 30, 70 will contour to the shape of the user's features and solidify upon cooling, such that support and/or immobilization to the arm, wrist, and hand are provided in a customized and personalized splint.

Referring to FIGS. 1-20, a second preferred embodiment of the present invention operates as follows. A user heats the support members 30, 70 to induce a suitable heat-forming temperature. Once the supports are heat-formable, the user may reshape and/or recontour the support members 30, 70 based on the nature of the user's injury and/or profile of the user's arm and hand. Immediately after reshaping and/or recontouring, a user places the support members 30, 70 in position within the pockets of the splint. The user is then able to immediately wear the splint with custom molded support members 30, 70.

Referring now to FIGS. 21-27 and 29-30, a dynamic traction attachment 100 may be provided as a separate add-on to the main body 20. The dynamic traction attachment may include an insert 128 that may detachably attach to a portion of the main body 20. The dynamic traction attachment 100 may further include an extension 102 attached to the insert 128 and that extends past a longitudinal end 124 of the main body 20 to cover a portion of some fingers on the hand the main body 20 is positioned on. In the illustrated embodiment, the extension 102 has an arcuate shape and overlies a back of the hand that is opposite from the palm of the hand. The extension 102 may have a greater transverse length than the insert 128 such that the extension 102 and insert 128 may be generally T-shaped. The extension 102 may also have a greater thickness than the insert 128. The extension 102 may comprise of two layers that sandwich a longitudinal end of the insert 128. However, those of ordinary skill in the art will appreciate from this disclosure that the extension may be a single layer that can be attached to the insert, or, the extension may be integrally formed with the insert such that the insert and extension are one-piece without departing from the scope of the current invention. If the extension is formed of two layers, the two layers may be formed out of different materials. For example, the inside layer facing the user's hand may be formed out of a softer material than the outside layer. Furthermore, those of ordinary skill in the art will appreciate from this disclosure that the extension 102 may not be detachably attached to the main splint body 20, but may be integrally formed with the splint main body 20 without departing from the scope of the current invention.

Figure 22:
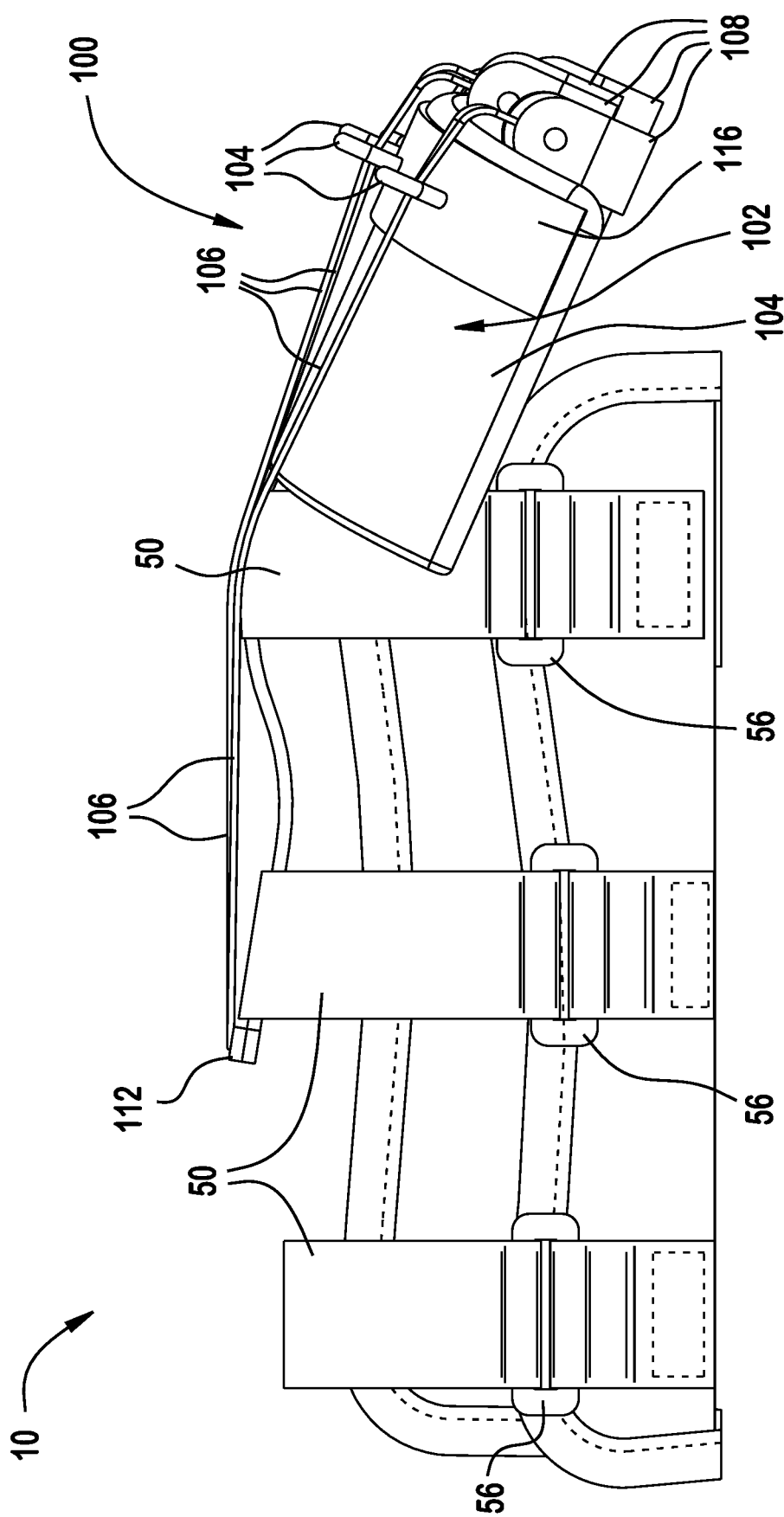
FIG. 22 is a right side view of the splint of FIG. 21. The extension may be slanted downward towards the arm. The finger slings may hold a finger inserted therein in the extended, semi-extended, or neutral position. Activation of muscles may allow a user to flex their fingers due to the line and/or finger sling being formed of an elastic material. An outer surface of the extension may have a second layer that can be attached thereto. The second layer may have loops built directly thereon or be configured to sandwich loops between it and the outer surface of the extension.

As best seen in FIG. 22, the extension 102 may be angled inward toward the hand. However, those of ordinary skill in the art will appreciate from Applicant's disclosure that the extension 102 may not be arcuate, may cover the palm of the hand instead of the back of the hand, and may be angled away from or be parallel to the hand without departing from the scope of the current invention. The extension 102 may be adjustable or bendable in order to change the angle.

Still referring to FIGS. 21-27 and 29-30, at least one finger sling 108 may be attached to the dynamic traction attachment 100, wherein the arcuate extension 102 is configured to locate the at least one finger sling 108 adjacent to a finger of the hand on which the main body 20 is positioned such that the finger can be placed inside the at least one finger sling 108. The term "adjacent" as used in the previous sentence means that the finger sling 108 can be located close enough to a fingertip that a user can place their finger within the finger sling 108. "Adjacent" as used in this paragraph may refer to when the splint 10 is fully positioned and secured on an arm, or when the splint 10 is being positioned and/or secured on the arm.

Figure 26:
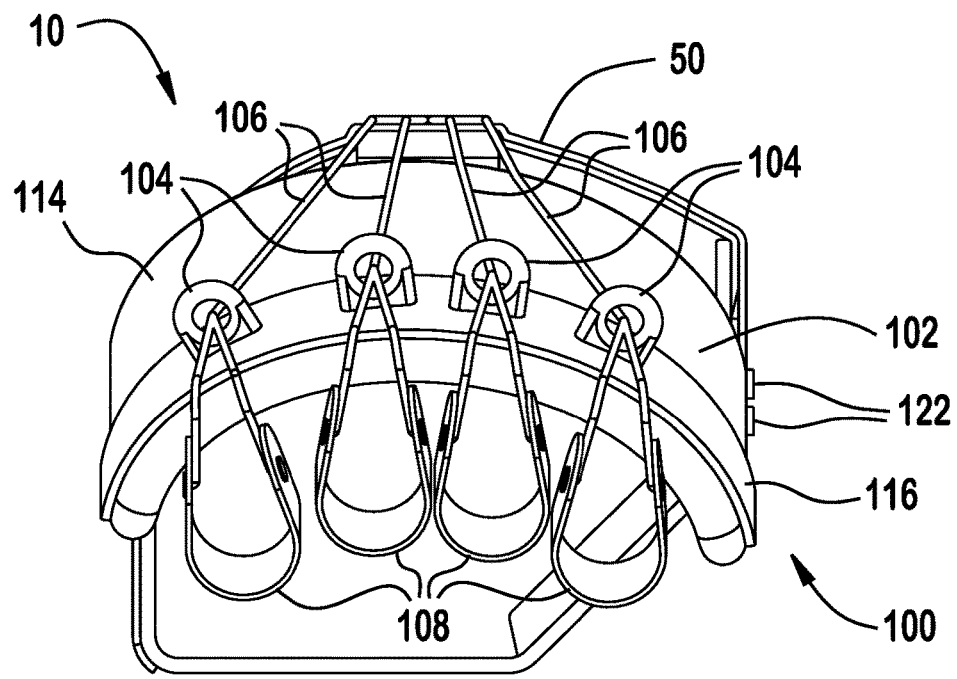
FIG. 26 is a front elevational view of the splint of FIG. 21. The loops may be movable on the outer surface of the extension so that positioning of the finger slings may be changed. The extension may further be moldable to allow customization and adjustment.
Figure 27:
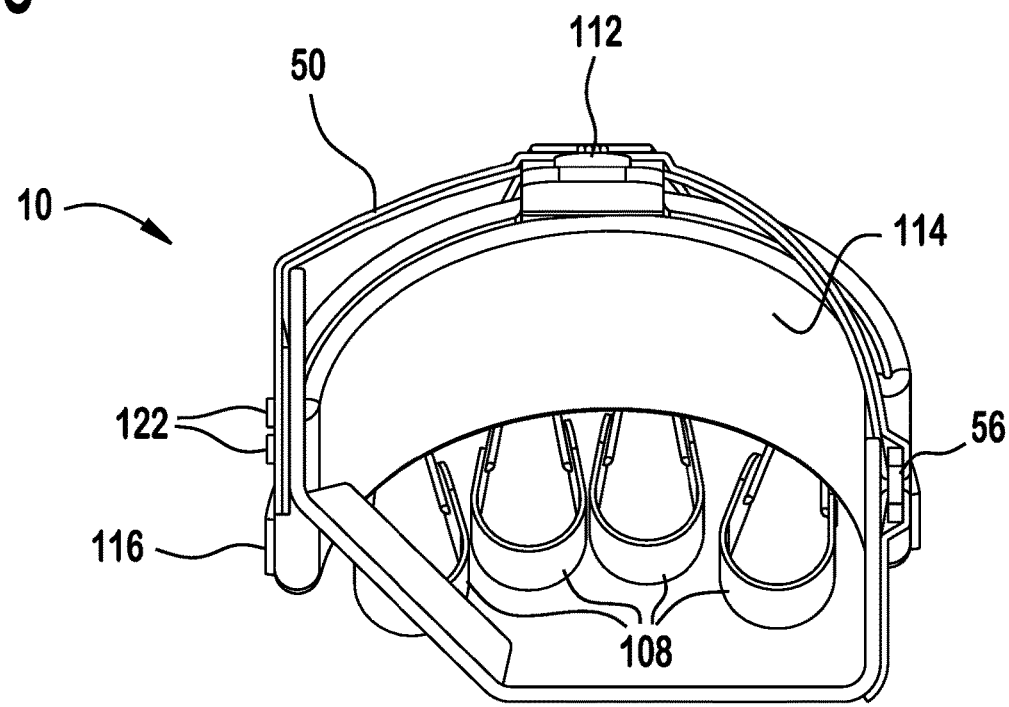
FIG. 27 is a rear elevational view of the splint of FIG. 21.

As best illustrated in FIGS. 22, 26, and 27, the finger slings 108 extend inward from the longitudinal end of the outer surface 114 of the extension 102 toward the fingers. The at least one finger sling 108 may be attached to the insert 128 or extension 102 by a line 106, wherein a first line end is attached to the insert 128 or extension 102 and a second line end is attached to the at least one finger sling 108. In the illustrated example, the second line end splits into two lines to support the finger sling 108 at two locations. However, those of ordinary skill in the art will appreciate from this disclosure that the finger sling 108 can be attached to the dynamic traction attachment 100 in any manner such that the finger sling 108 is located adjacent to a finger. For example, a portion of the finger sling 108 may be directly attached to the extension 102 without the use of any lines, or the finger sling 108 may be supported by the line 106 at only one location. Furthermore, those of ordinary skill in the art will appreciate from this disclosure that each line 106 may be a combination of multiple lines and/or materials, for example, a first portion of the line may be elastic while a second portion of the line may be relatively inelastic. In addition, the line 106 may comprise a rubber band with relatively inelastic lines attached thereto.

Figure 30:
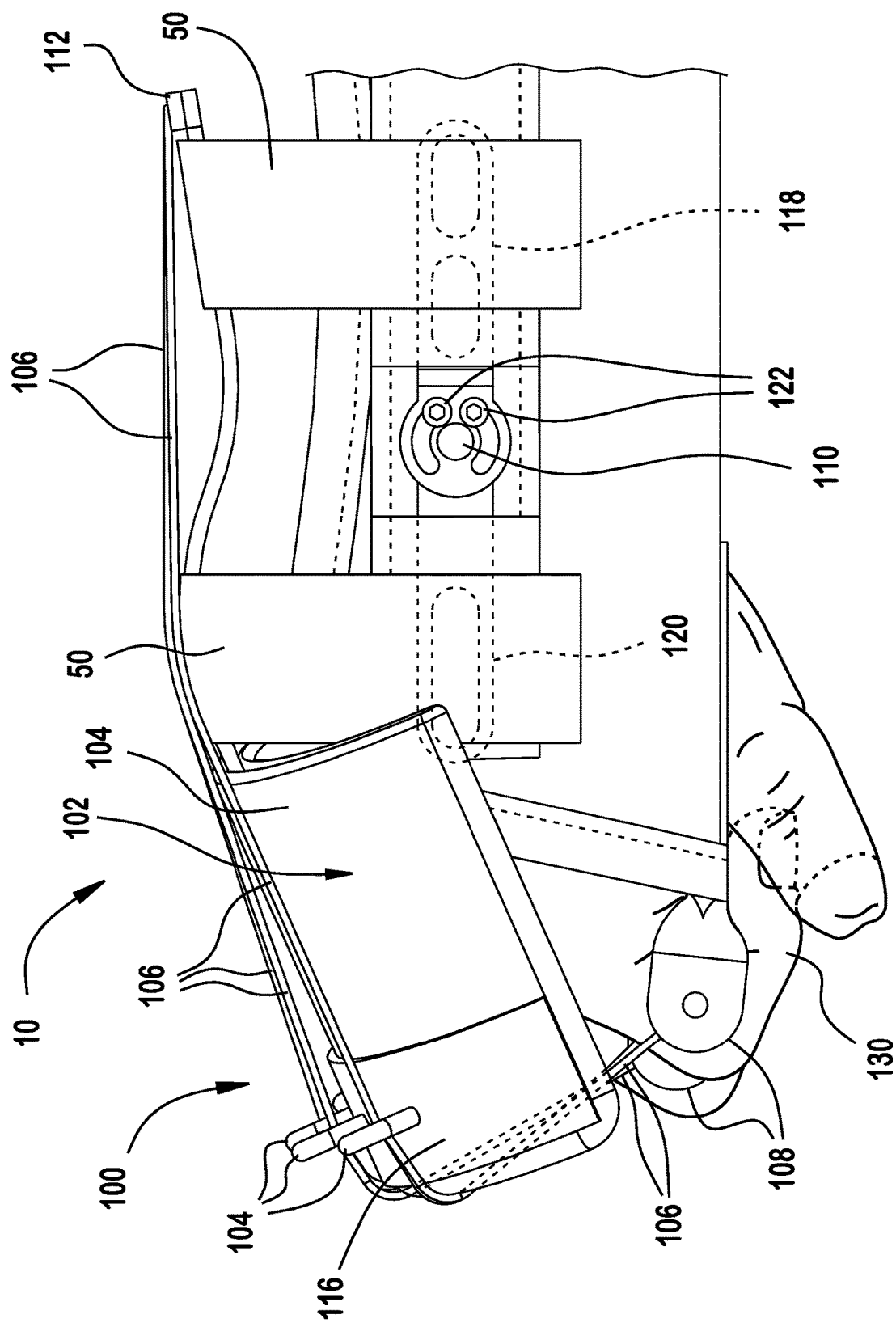
FIG. 30 is a view of FIG. 29 with the fingers in the flexed position. The user has moved their fingers in the flexed position by preferably activating their muscles. Upon moving of the fingers from the extended, semi-extended, or neutral state to the flexed state the user may overcome the elasticity force of the line and/or finger sling thereby stretching the line and/or finger sling. Upon deactivation of the arm muscles, the elasticity force of the line and/or finger slings will return the finger slings towards the free state position. A longitudinal end of the extension may be rounded so that the line, which extends thereover, does not slide against or rub a relatively sharp edge while stretching and contracting.

At least one of the line 106 and the finger sling 108 may be elastic thereby allowing dynamic flexion and extension of the finger that is inside the at least one finger sling 108. For example, if the extension 102 is positioned so as to cover a back of the hand (opposite of the palm), as in FIG. 29, it is preferable that in the free state the finger sling 108 is located such that when a finger 130 is placed inside the finger sling 108, and the person is not activating his arm/hand muscles, that the finger 130 is kept in the extended, semi-extended, or neutral position. Therefore, flexion of the finger 130, as illustrated in FIG. 30, stretches the elastic line 106 and/or finger sling 108, and, returning the finger 130 from the flexed state to the extended, semi-extended, or neutral state returns the elastic line 106 and/or finger sling 108 back to its free state. Therefore, it is preferable that the elasticity of the line 106 and/or finger sling 108 is such that the line and/or finger sling will not significantly stretch due solely to the weight of a finger inserted in the finger sling 108 (without activation of the proper muscles). Contrarily, if the extension 102 is positioned to cover the palm of the hand then extending the fingers would stretch the elastic line 106 and/or finger sling 108 and movement of the finger from the extended state to the flexed, semi-flexed, or neutral state would return the elastic line 106 and/or finger sling 108 back to its free state position. The dynamic traction of a single or multiple digits may be used to treat extensor or flexor tendons post repair for dynamic motion as well as stenosing tenosynovitis and arthrosis such as rheumatoid disease of the extensor mechanism as well as the MP, and PIP joints. In addition, the at least one of the elastic line 106 and/or finger sling 108 may be removed and replaced by a line 106 and/or finger sling 108 with a different elasticity and/or length. As such, the dynamic traction attachment 100 may allow dynamic protected motion and/or protected partial motion of the fingers and/or thumb as opposed to rigid immobilization. Similarly, the hinge 110 may provide for the splint to allow partial protected motion of the wrist and/or hand and/or forearm as opposed to using rigid immobilization. Depending on the ailment, this can speed recovery and rehabilitation while reducing potential atrophy of parts of the body due to rigid immobilization.

If the finger sling 108 is attached to the dynamic traction attachment 100 by a line 106, the extension 102 may include at least one loop 104 thereon. The loop 104 is preferably located between the first line end that is attached to the dynamic traction attachment 100 and a longitudinal end of the outer surface 114 of the extension 102 such that the line 106 is configured to extend through the loop 104. The loop 104 may be configured to assist in locating the at least one finger sling 108 adjacent to the finger. For this purpose, it is preferable, although not necessary, that the loop 104 be positioned adjacent to the longitudinal end of the outer surface 114 of the extension 102, wherein the term "adjacent" as used in this sentence means that the loop 104 is preferably positioned within three inches of the longitudinal end of the extension 102, and more preferably, positioned within an inch of the longitudinal end of the extension 102. Those of ordinary skill in the art will appreciate from this disclosure that the loop 104 is not necessary to assist in locating the finger sling 108 adjacent to a finger, and that the line 106 and/or finger sling 108 may be guided towards a finger by any suitable means without departing from the scope of the invention. In addition, those of ordinary skill in the art will appreciate that guiding the finger sling 108 and/or line 106 towards a finger may be omitted altogether without departing from the scope of the invention. If guiding means are omitted, it is preferable, but not necessary, that the finger sling 108 and/or line 106 is fixed to the insert 128 or extension 102 as close as possible to the longitudinal end of the extension 102. Those of ordinary skill in the art will further recognize that the finger slings 108 and/or lines 106 may be attached directly to the main splint body 20 such that no insert 128 or extension 102 is required.

In the illustrated embodiment, four finger slings 108 are connected to the insert 128 by four separate and respective lines 106, and wherein each line 106 extends through one of the four hoops 104 provided on the extension 102 such that each finger sling 108 is located adjacent to a different finger. Each finger sling 108 is configured to receive only a single finger. However, those of ordinary skill in the art will appreciate from this disclosure that the finger slings 108 may be configured to receive more than one finger without departing from the scope of the invention.

Still referring to FIGS. 21-27 and 29-30, the loops 104 may have fixing portions 126 that are configured to fix the loops 104 to the extension 102. The fixing portions 126 may be designed to follow the contour of the outer surface 114 of the extension 102. Since the extension is preferably moldable and can be re-shaped, it is preferable that the fixing portions 126 can be bendable. A second layer 116 may be configured to be attached to the outer surface 114 of the extension 102 such that the second layer 116 sandwiches the fixing portions 126 between the outer surface 114 of the extension 102 and the second layer 116; thereby fixing the at least one loop 104 on the extension 102. The second layer 116 may comprise slits therein to allow the loops 104 to extend through the second layer 116. The second layer 116 may be attached to the outer surface 114 by adhesive, Velcro, snaps, or any other suitable means. Therefore, the loops 104 may, but not necessarily, be configured to be movably positioned at different locations on the extension 102 in order to locate the finger slings 108 closer to the fingers, or, vary the angle of the line 106 with respect to a finger. Therefore, a specially designed dynamic elastic band traction apparatus may complement the dynamic/ie-shapeable insert 128, extension 102, and/or support members 30 and can be customized in angle or application of the forces on the digits.

Those of ordinary skill in the art will appreciate from this disclosure that the loops 104 may be unremovably fixed to the second layer 116 or the outer surface 114 of the extension 102, thereby eliminating the need for the second layer 116 to sandwich a portion of the loops 104, without departing from the scope of the invention. Those of ordinary skill in the art will further recognize that the loops 104 may be movably positioned on the outer surface 114 of the extension 102 without the use of the second layer 116 without departing from the scope of the invention. For example, the loops may be fixed to the outer surface 114 of the extension 102 by magnets, snaps, Velcro, or any other suitable means.

Figure 21:
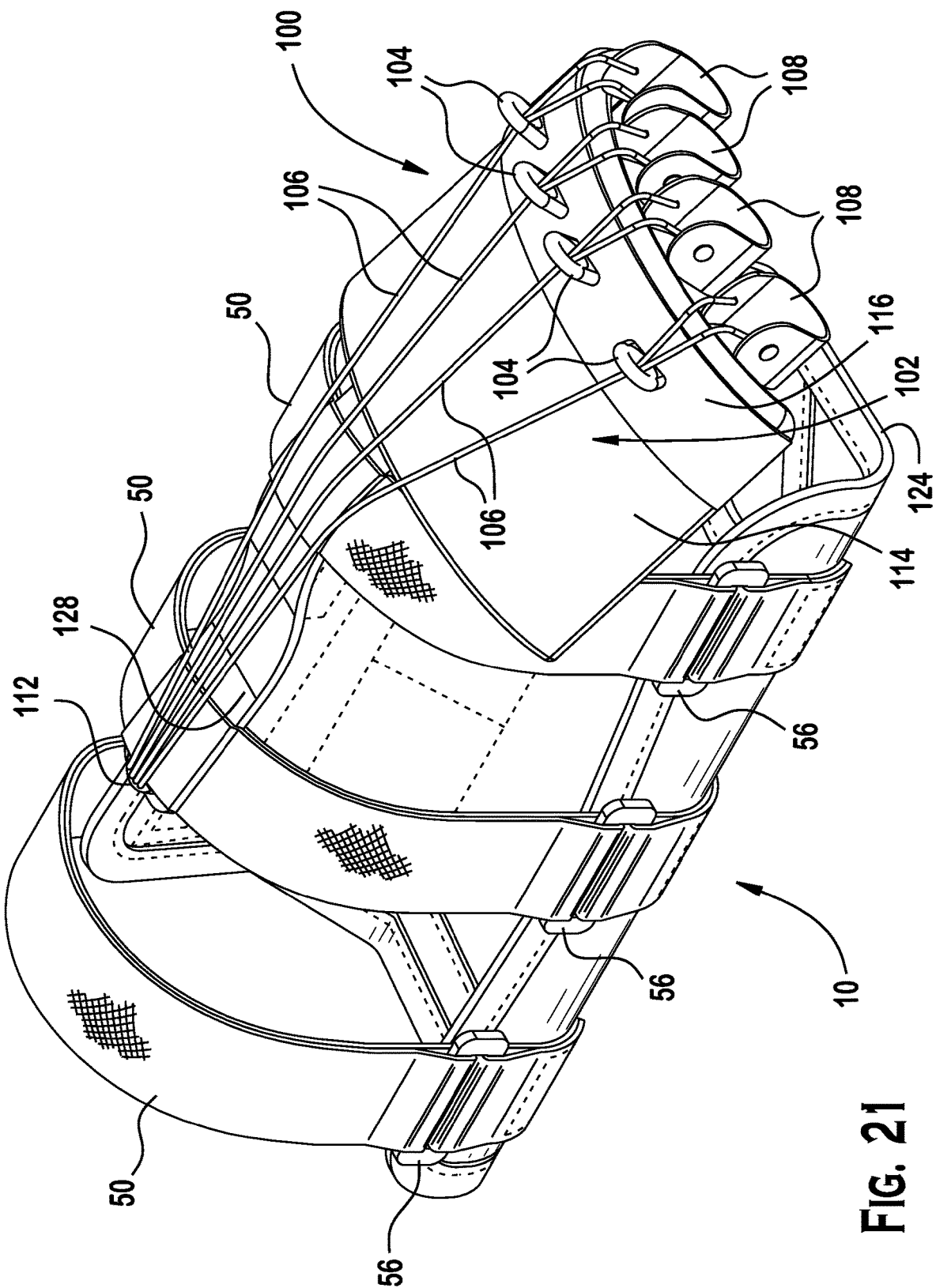
FIG. 21 is a perspective view of a third preferred embodiment of the splint of the present invention. The splint may comprise a dynamic traction attachment attached to the straps of the main splint body. A strap may be comprise two layers. The dynamic traction attachment may comprise an insert that may be attached to the straps by extending in the middle of the two layers of the strap such that a portion of the insert is sandwiched between the two layers. A protrusion on the insert may abut a strap to prevent movement of the insert in at least one longitudinal direction. An arcuate extension may be connected to the insert and extend past a longitudinal end of the main splint body to cover a portion of hand. The insert and extension may generally be T-shaped. Lines may extend from the protrusion and support finger slings that are configured to be positioned adjacent to a finger. The arcuate extension may aid in locating the finger slings adjacent to fingers. The arcuate extension may have loops thereon that are adjacent to the longitudinal end of the extension. The lines may be configured to extend through the loops such that the loops further help to position the finger slings adjacent to a finger.

As illustrated in FIG. 21, the insert 128 is detachably attached to the straps 50. At least one strap 50 may be double-layered and the insert 128 may be attached to the main body 20 by positioning it in the middle of the two layers such that a portion of the insert 128 is sandwiched by the double-layered strap 50. However, those of ordinary skill in the art will recognize from this disclosure that the insert 128 may be inserted in a pocket or attached to any other portion of the main body 20 by any suitable means such that the dynamic traction attachment 100 is able to locate a finger sling 108 adjacent to a finger.

As illustrated in FIGS. 21-24, the insert 128 may further comprise a projection 112 thereon. The projection 112 may project outwardly away from a user's arm and is configured to abut a strap 50 of the splint 10 so as to fix the dynamic traction attachment 100 in at least a longitudinal direction with respect to the main body 20. In addition, the projection 112 may be configured to secure the first line end of each line 106. However, those of ordinary skill in the art will appreciate that the sling may be fixed in the longitudinal direction by any other suitable means and the first line ends may be fixed to another part of the dynamic traction attachment 100, such as the extension 102, without departing from the scope of the current invention. Furthermore, the projection may extend inward towards a user's arm. In such a case, the lines 106 may be configured to extend along an inner surface of the insert 128 and/or extension 102, and, loops 104 may also extend inward from an inner surface of the extension 102 to locate the finger slings 108 adjacent to a user's fingers.

Similarly to the support members 30, the insert 128 and/or the extension 102 may be configured to be heat-formed such that upon heating, the insert 128 and/or extension 102 may be re-shaped to be custom fitted to the user. For example, the insert 128 may be molded at multiple angles to allow optimal position to allow the correct traction and tension for the particular injury. The user may fix the insert 128 into position on the splint 10, heat the splint and insert 128, and then place the splint in position on the user's arm/hand so that the insert 128 forms and cools to the shape of the user. However, those of ordinary skill in the art will appreciate from this disclosure that the insert 128 and/or extension 102 may be heated and re-shaped prior to being fixed to the splint 10.

The insert 128 and/or extension 102 may be formed out of a thermoplastic material that becomes soft when heated and hard when cooled, therefore a user may easily adjust the shape and/or contour whenever needed. However, those of ordinary skill in the art will appreciate from this disclosure that the insert 128 and/or extension 102 may be formed out of any material whose shape and/or contour may be adjusted. For example, the insert 128 and/or extension 102 made be formed of a flexible material that can be bended at room temperature. It may be preferable for the insert 128 and extension 102 to be formed out of two different materials. For example, the insert 128 may be formed out of a thermoplastic material while the extension 102 is formed out of a softer and/or more flexible material. If the insert 128 is formed of a thermoplastic material, it is preferably that the insert 128 and/or extension 102 can be heated using common appliances, such as a microwave, stove, oven, or dryer, so that the insert 128 and/or extension 102 can be heated and re-shaped quickly in any location having a common appliance. In one embodiment the entire splint 10, including all attachments and/or inserts including the dynamic traction attachment can be heated in a microwave and then put on a user's hand for final precise configuration. This allows the insert 128 and/or extension 102 to allow optimal position of the finger slings, thereby allowing the correct traction and tension for the particular injury. The insert 128 and/or extension 102 can preferably be re-shaped and/or re-contoured repeatedly so that they can be adjusted to the patient and condition being treated through specific molding and utilizationof the pieces with progressive odi cati ons throughout the healing and treatment process. In addition, the splint, dynamic traction attachment 100, and support members 30 can be re-customized for a different person and/or injury. The dynamic traction attachment 100 and support members 30 are preferably configured to be repeatedly re-shaped and/or re-contoured without the use of any tools except a heating source. The insert 128 may, but not necessarily, be made out of the same material and have the same general shape as one of the support inserts 30.

Additionally, an insert can be attached for use with the thumb of the splint wearer. The thumb splint can include additional material and or dynamic elements. Similar to the dynamic traction attachment, the thumb insert can include padded material and a traction component or the like. Alternatively, the dynamic traction attachment can be modified to also include to provide a finger sling for a thumb.

Still referring to FIGS. 21-27, the insert 128 may be formed by an elongated member that is generally aligned parallel to a longitudinal axis of the splint. The axis is generally aligned with a longitudinal axis of the arm 12 of the user. However, those of ordinary skill in the art will appreciate from this disclosure that any size and shape insert 128 may be used without departing from the scope of the present invention. Those of ordinary skill in the art will further appreciate from this disclosure that the insert 128 may be omitted altogether without departing from the scope of the present invention. For example, the extension 102 may be detachably attached directly to the main splint body 20 without an insert, or the extension 102 may be integrally formed with the main splint body 20.

Figure 23:
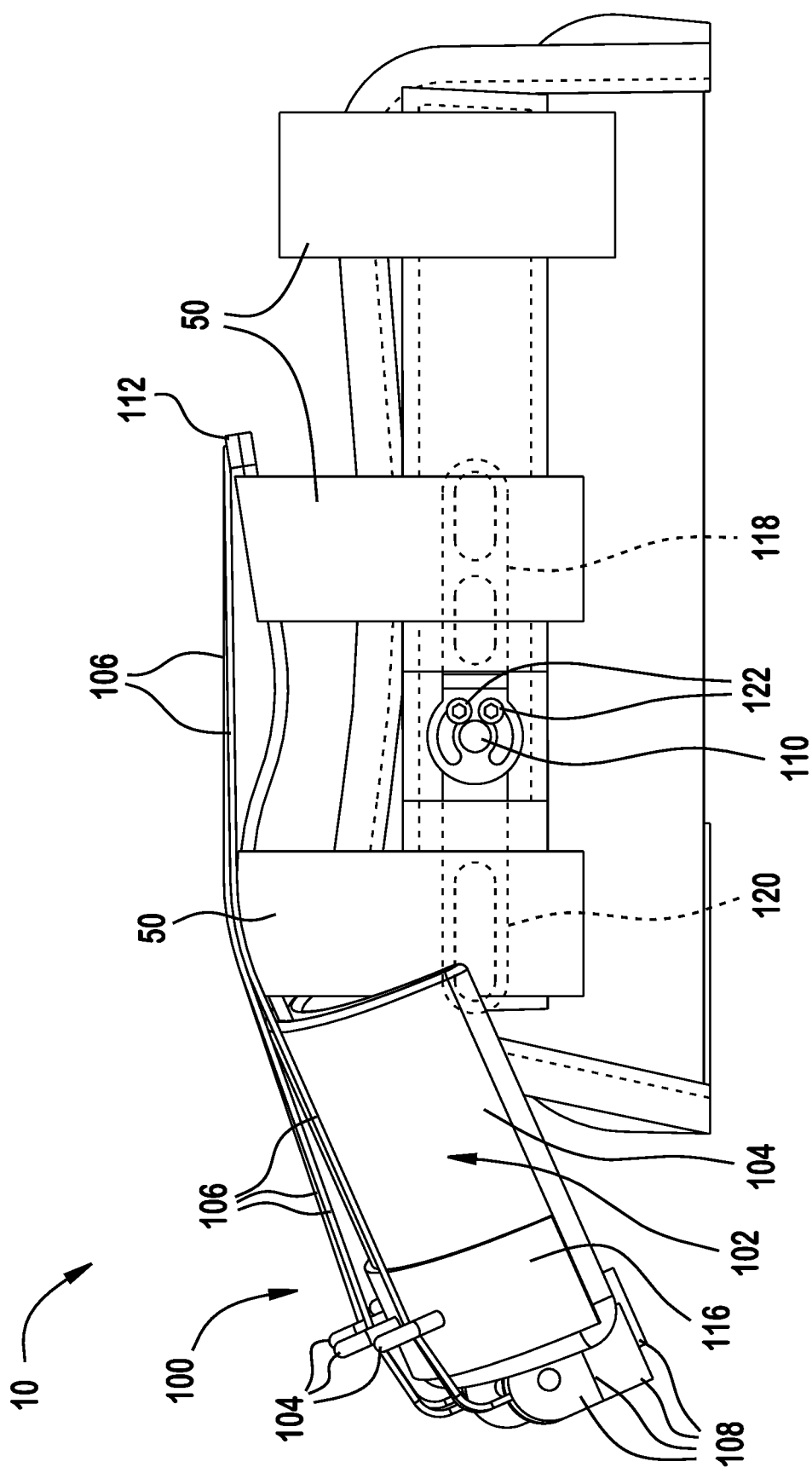
FIG. 23 is a left side view of the splint of FIG. 21. The insert may have a curved shape. At least one of the insert and extension may be moldable and adjustable such that the insert and/or extension can be re-shaped. Preferably the insert and/or extension can be re-shaped after being heated. The splint may further comprise a hinge thereon. The hinge may have first and second legs extending from a center portion thereof. The first and second legs may be configured to be inserted into respective hinge pockets formed in the main splint body. A first hinge pocket may be located on a portion of the main splint body that is configured to cover or overlap a portion of a forearm, and, a second hinge pocket may be located on a portion of the main splint body that is configured to cover or overlap a portion of a hand. When the first and second legs are inserted into their respective hinge pockets, the center portion of the hinge may be configured to be fixed to a portion of the main splint body that covers or overlaps a portion of a wrist. The hinge may be configured to either lock the first leg at various angles with respect to the second leg, thereby locking the wrist and various angles with respect to the forearm, or allow a pre-determined range of motion of the hand with respect to the forearm (e.g. the hinge allows the wrist to freely extend and/or flex a predetermined angle before preventing further extension and/or flexion). The hinge may allow radial and ulnar deviation. The hinge may have locking nuts configured to lock the first leg with respect to the second leg, or, limit the range of motion of the first leg with respect to the second leg.
Figure 24:
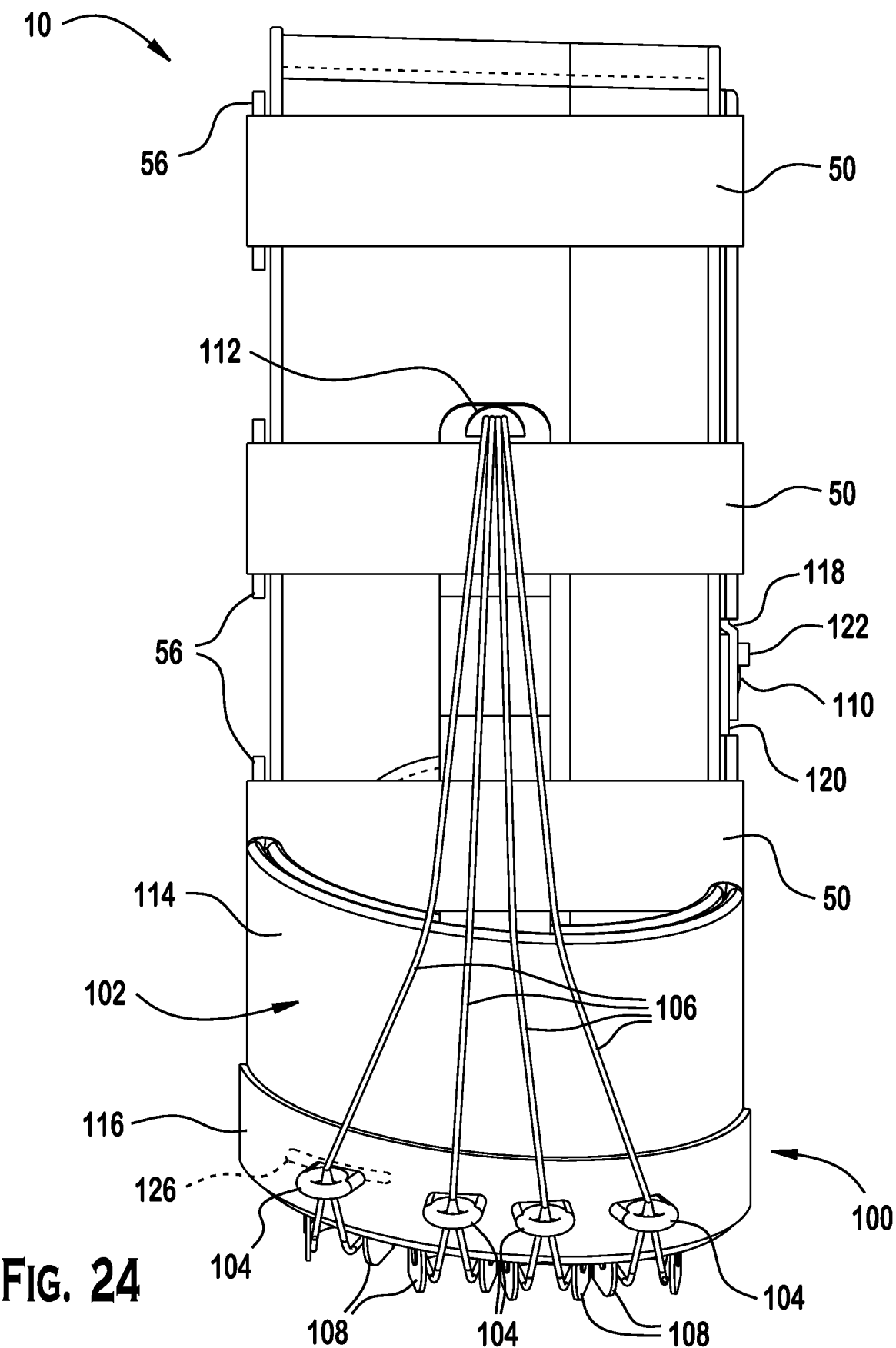
FIG. 24 is a top plan view of the splint of FIG. 21. A first end of each line may be attached to the projection of the insert while the second end of each line may split into two separate lines that each support a single finger sling. The lines and/or finger slings may be removed and replaced so that different elasticities and/or lengths may be provided. The main body of the extension may be formed out of a relatively soft material with respect to the second layer placed thereon. Alternatively, an inside surface of the extension may be formed of a soft material while the outer surface of the extension may be formed out of a different, possibly relatively harder, material.
Figure 25:
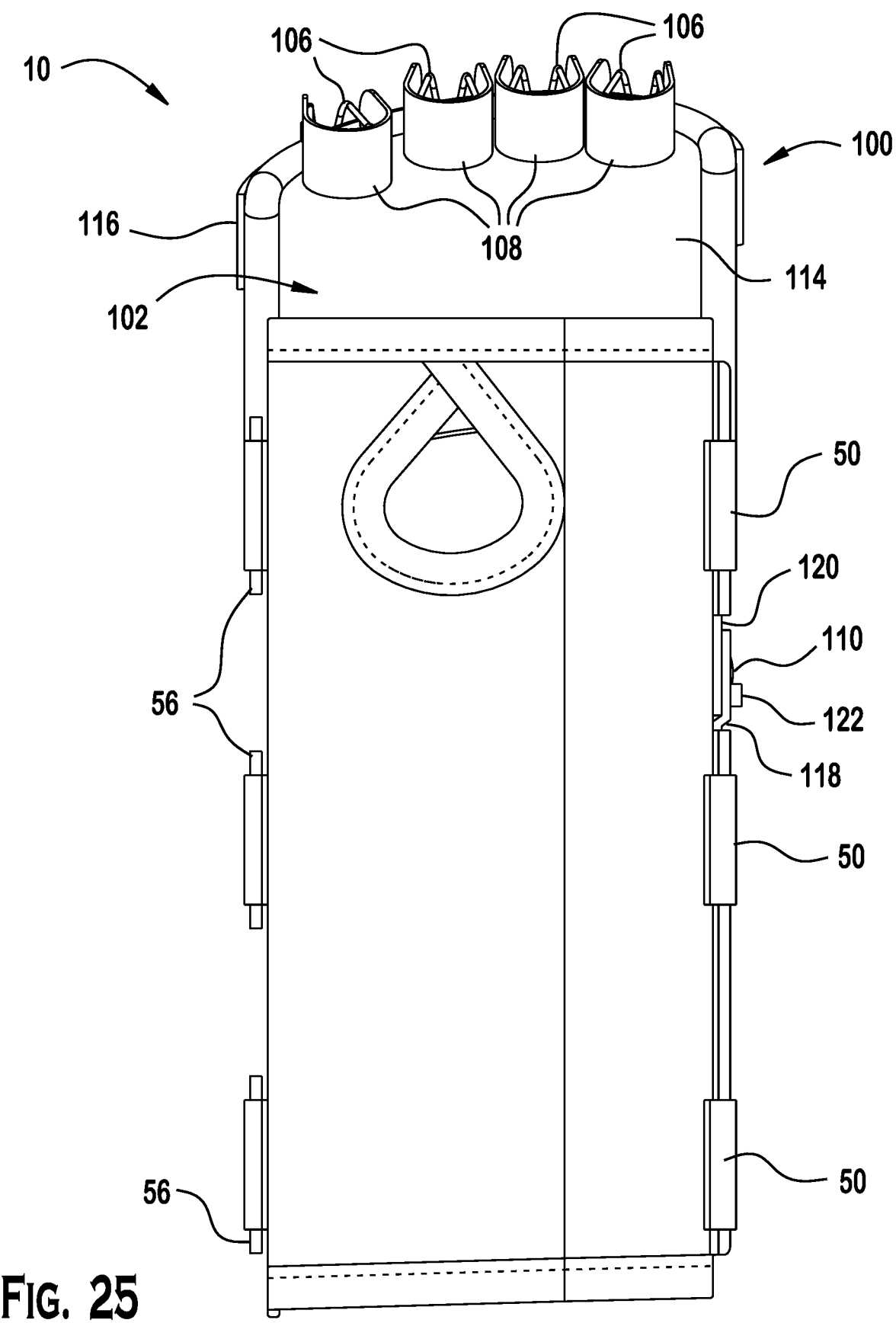
FIG. 25 is a bottom plan view of the splint of FIG. 21. The extension may extend past a longitudinal end of the main splint body. A longitudinal end of the extension may be curved so that expansion and contraction of the lines do not rub against sharp corners.
Figure 28:
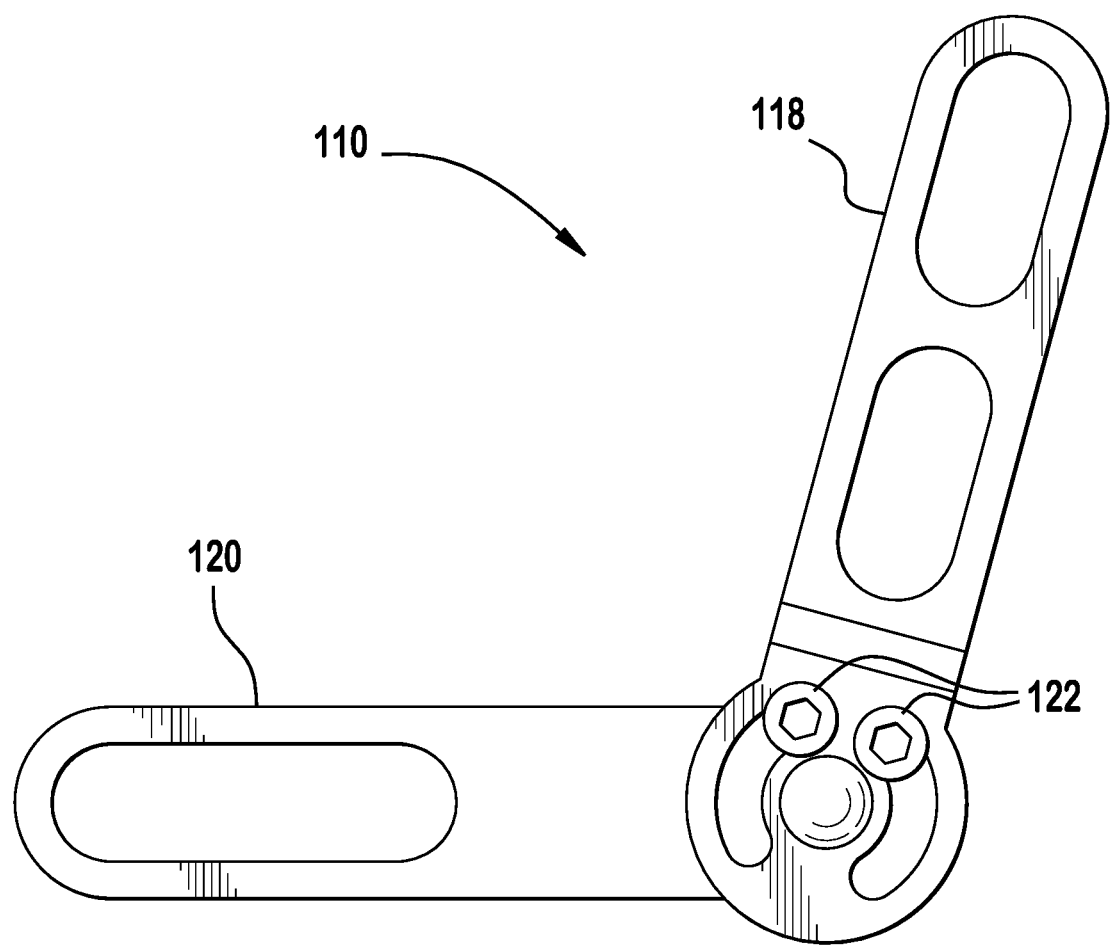
FIG. 28 is a front view of the hinge used in the splint of FIG. 21. First and second legs extend from a circular center portion. The circular center portion provided with locking nuts to lock the first and second legs at various angles with respect to each other.
Figure 29:
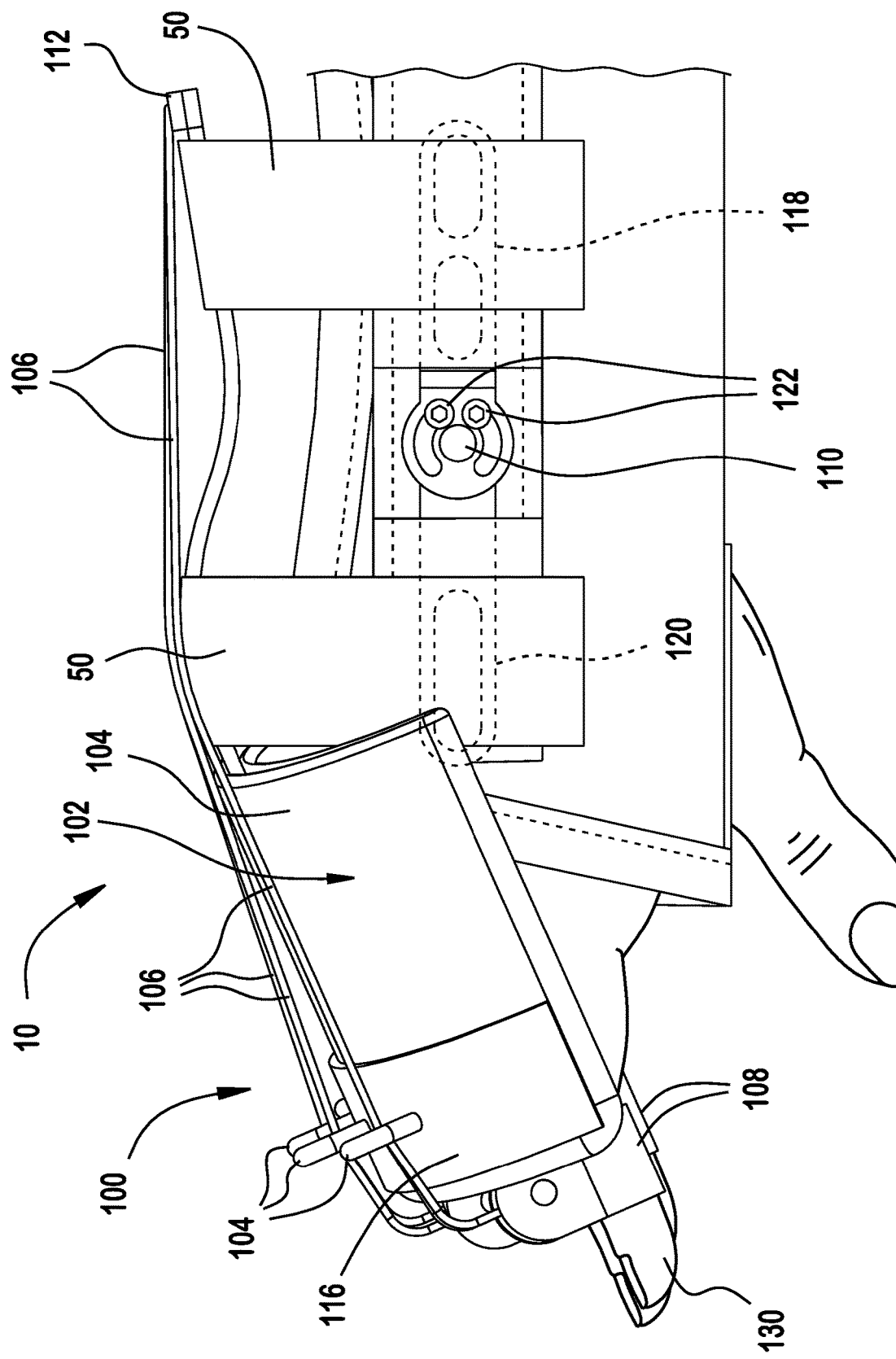
FIG. 29 is a left side view of the splint of FIG. 21 positioned on a user's arm. Each finger may be placed into a respective finger sling that may be attached to the dynamic traction attachment by lines. In the free state, the lines and finger slings may be configured such that, when the user is not activating any arm muscles, the finger slings keep the fingers in the extended, semi-extended, or neutral position. In the free state, the lines may be configured to have no slack therein.

As illustrated in FIGS. 23 and 28, the splint may comprise a hinge 110 that may have first and second legs 118, 120 extending from a center portion thereof. The first leg 118 may be configured to be removably positioned on a first main splint body portion that covers a portion of the forearm. The second leg 120 may be configured to be removably positioned on a second main splint body portion that covers a portion of the hand. The center portion may be configured to be removably positioned on a third main splint body portion that covers the wrist. The first, second, and third main splint bodies may be located at any circumferential location of the main splint body 20. For example, the hinge 110 may be positioned on either side of the arm/wrist/hand or be positioned on the bottom of the arm/wrist/hand such that the second leg 120 of the hinge 110 covers the palm of the hand. The hinge 110 may be configured to lock the first leg at various angles with respect to the second leg thereby locking the hand at various angles with respect to the forearm. Locking nuts 122 may be provided on the center portion of the hinge 110 to lock the first and second legs 118, 120 at various angles. However, those of ordinary skill in the art will appreciate that any suitable locking mechanism may be used to lock the first and second legs 118, 120 at various angles.

The hinge 110 may allow complete rigid immobilization of the wrist or allow a pre-determined range of motion of the wrist (e.g. allows at least one of flexion and/or extension of the wrist up to a pre-determined angle). For example, preferably one embodiment of the hinge 110 allows flexion and/or extension of the wrist within a range of one-hundred fifty degrees. Preferably another embodiment of the hinge 110 allows flexion and/or extension of the wrist within a range of one-hundred twenty degrees. Preferably another embodiment of the hinge 110 allows flexion and/or extension of the wrist within a range of ninety degrees. Preferably another embodiment of the hinge 110 allows flexion and/or extension of the wrist within a range of sixty degrees. Preferably another embodiment of the hinge 110 allows flexion and/or extension of the wrist within a range of thirty degrees. Preferably another embodiment of the hinge 110 allows flexion and/or extension of the wrist within a range of fifteen degrees. Preferably another embodiment of the hinge 110 allows flexion and/or extension of the wrist within a range of ten degrees. Preferably another embodiment of the hinge 110 allows flexion and/or extension of the wrist within a range of five degrees. Those of ordinary skill in the art will appreciate from this disclosure that the range of motion allowed by the hinge 110 may be set at any range between zero degrees and one-hundred eighty degrees without departing from the scope of the current invention. The hinge 110 preferably, but not necessarily, is rigid in its flexion and extension protection but allows some flexibility in the radial and ulnar deviation. The hinge 110 may be metal or plastic. Special pockets may be provided in the main body 20 to receive the first and second legs 118, 120 therein.

The hinge 110 may further comprise at least one of the first leg 118 and the second leg 120 having a hinge contour that is configured to be adjusted at least one of immediately prior to being positioned on the main splint body 20 and after being positioned on the main splint body 20 such that the hinge contour can be customized to the person. The hinge 110 may further be configured to be heat-formed such that upon heating, the hinge 110 may be adjusted and contoured to the specific shape of the arm 12, wrist 14, and hand 16 of the user. Preferably, the user may insert the hinge 110 into the pockets, heat the splint and hinge 110, and then place the splint in position on the user's arm so that the hinge 110 forms and cools to the shape of the user's arm, wrist, and/or hand. However, those of ordinary skill in the art will appreciate from this disclosure that the hinge 110 may be heated and re-shaped immediately prior to being inserted into the pockets, wherein "immediately prior" as used in this sentence is defined as within thirty minutes such that the hinge 110 may be heated and re-shaped during the appointment time of a user such that at the end of the appointment the user may have a splint with a custom-shaped hinge 110. More preferably, "immediately prior" means that the hinge 110 may be heated and re-shaped within fifteen minutes such that the entire process can take place during the appointment time of a user such that at the end of the appointment the user may have a splint with a custom-shaped hinge 110. More preferably, "immediately prior" means that the hinge 110 may be heated and re-shaped within ten minutes. More preferably, "immediately prior" means that the hinge 110 may be heated and re-shaped within five minutes. More preferably, "immediately prior" means that the hinge 110 may be heated and re-shaped within two minutes.

The hinge 110 may be formed out of a thermoplastic material that becomes soft when heated and hard when cooled, therefore a user may easily adjust the shape and/or contour whenever needed. However, those of ordinary skill in the art will appreciate from this disclosure that the hinge 110 may be formed out of any material whose shape and/or contour may be adjusted. Preferably, the hinge 110 can be heated using common appliances, such as a microwave, stove, oven, or dryer, so that the hinge 110 can be heated and re-shaped quickly in any location having a common appliance. The pockets for the hinge 110 may be lined with an insulating material so that a user is not burned while positioning the splint 10 with a heated hinge 110 on their arm, wrist, and/or hand. As such, the hinge 110 can be conveniently and quickly reshaped and/or resized to follow the contour of the user's arm and hand.

The hinge 110 may further include a torsion spring. The torsion spring may be configured to apply a torsion force when the wrist moves in at least one of the extension direction or the flexion direction.

A splint 10 including at least one of, or a combination of, the adjustable support members 30, 70, the adjustable dynamic traction attachment 100 with finger slings 108, and the hinge 110 may be provided to treat at least the following conditions: Post-operative dynamic protected motion after surgical repair of nerve and tendon repair of the hand, wrist and digits allowing the institution or early protected motion; Lunatotriquetral Ligament Injuries and wrist and hand fractures; Fractures of the phalanges, metacarpals and wrist and forearm; Extensor and flexor tendon zone 2, 3 and 4 injury and lacerations; Finger tendinitis and stenosing tenosynovitis; rigger fingers; Rheumatoid arthritis of the hand and wrist; Carpal Tunnel Syndrome (without surgery); Repetitive Strain Injury; Extensor and flexor tenosynovitis (tendinitis at the wrist and forearm); Lateral and medial epicondylitis at the forearm and elbow; tunnel; Wrist and hand arthritis; Synovitis of the wrist; Ligament injury of the wrist, scapholunate, lunatotriquetral; Triangular fibrocartilage complex (TFCC) and scapholunate ligament tears; Radio-ulnar joint injury; Arthritis of the fingers, MP and PIP joints, wrist and radioulnar joint; Tennis elbow; Forearm, wrist and hand tendinitis. In addition, the support members 30, 70, dynamic traction attachment 100, location of the finger slings 108, and hinge 110 may be adjusted or modified as the needs of the patient change throughout the healing process. Specifically, the device is fully adjustable by reshaping, removing, adding, and changing the main stay pieces for maximum adaptation to the patient. Furthermore, the splint can place the wrist in an extended or cock up position, and, allow stabilization and immobilization of the fingers in extension or flexion.

The support members 30, 70, hinge 110 and dynamic traction pieces 102/128/108 included are customizable and adjusted to the patient and condition being treated through specific molding and utilization of the pieces with progressive modifications throughout the healing and treatment process. The device is specifically designed to immobilize the fingers, wrist and hand to a variety of positions and rigidities according to the nature of the injury and the stage the patient has reached in the healing process. The adjustability of all the pieces allows for maximum adaptation to the patient for optimal control and comfort. In addition, the dynamic traction pieces may allow protected partial motion of the digits and thumb as opposed to rigid immobilization.

However, for some injuries it may be preferred that the dynamic traction pieces may only be configured as a support piece for resting the fingers and/or thumb. In such a case the finger slings 108 may be configured to support the fingers and/or thumb with semi-rigid or rigid immobilization. Those of ordinary skill in the art will recognize that the fingers slings 108 may be replaced and/or supplemented with the adjustable band 72, illustrated in FIG. 12, or the like, for the purpose of supporting the fingers. A portion of the insert 128 and/or extension 102 may be heatable and moldable, or bendable, in order to allow various resting positions of the fingers and/or thumb. The various resting positions allow the finger slings 108, adjustable band 72, and/or other support piece to treat various conditions such as healing tendinitis, arthritis or fractures.

Referring to FIGS. 21-30, a third preferred embodiment of the present invention operates as follows. A main splint body may be provided and configured to be positioned around the portion of the arm such that the splint extends longitudinally over: at least a portion of a forearm, over a wrist, and over a portion of a hand. A dynamic traction attachment may be provided that is configured to detachably attach to the main splint body. The dynamic traction attachment may include an arcuate extension. The arcuate extension may be configured to extend past a longitudinal end of the main splint body to cover a portion of some fingers of the hand on which the main splint body is positioned over. At least one finger sling may be attached to the dynamic traction attachment. The arcuate extension may be configured to locate the at least one finger sling adjacent to a finger of the hand on which the main splint body is positioned over such that the finger can be placed inside the at least one finger sling.

Referring to FIGS. 1-30, a fourth preferred embodiment of the present invention operates as follows. A main splint body may be provided and configured to be positioned around the portion of the arm such that the splint extends longitudinally over: at least a portion of a forearm, over a wrist, and over a portion of a hand. A dynamic traction attachment may be provided that is detachably attached to the main splint body. Support members may be removably inserted into pockets on the main splint body. The support members and a portion of the dynamic traction attachment may moldable or re-shapeable upon being heated. The main splint body, including the dynamic traction attachment and the support members, may be heated, for example in a microwave. After being heated, the splint may be positioned on the user's arm. After being positioned on the user's arm, the contour and shape of the users arm may adjust the contour or shape of the support members and/or the portion of the dynamic traction attachment. In addition, the dynamic traction attachment may be further bent into a preferred position if so desired. Upon cooling, the support members and/or portion of the dynamic traction attachment may maintain their shape.

It is recognized by those skilled in the art that changes may be made to the above described methods without departing from the broad inventive concept thereof. It is understood, therefore, that this invention is not limited to the particular embodiments disclosed, but is intended to cover all modifications which are within the spirit and scope of the invention as defined by the above specification, the appended claims and/or shown in the attached drawings.

What is claimed is:

1. A splint adapted for use on at least a portion of an arm of a person, the splint comprising:
    a main splint body configured to be positioned around the portion of the arm such that the splint extends longitudinally over: at least a portion of a forearm, over a wrist, and over a first portion of a hand;
    a dynamic traction attachment that is configured to detachably attach to the main splint body, the dynamic traction attachment comprising an arcuate extension, the arcuate extension configured to extend past a longitudinal end of the main splint body to cover a portion of some fingers of the hand on which the main splint body extends over; and
    at least one finger sling attached to the dynamic traction attachment, wherein the arcuate extension is configured to locate the at least one finger sling adjacent to a finger of the hand on which the main splint body extends over such that the finger can be placed inside the at least one finger sling;
    wherein the at least one finger sling is attached to the dynamic traction attachment by a line, wherein a first line end is attached to the dynamic traction attachment and a second line end is attached to the at least one finger sling.

2. The splint of claim 1, wherein the arcuate extension comprises at least one loop thereon, the at least one loop being located between the first line end that is attached to the dynamic traction attachment and an arcuate extension longitudinal end such that the line is configured to extend through the at least one loop, the at least one loop configured to assist in locating the at least one finger sling adjacent to the finger.

3. The splint of claim 2, wherein at least one of the finger sling and the line is elastic thereby allowing flexion and extension of the finger that is inside the at least one finger sling.

4. The splint of claim 3, wherein the splint comprises a plurality of finger slings, lines, and loops, wherein each of the plurality of finger slings is configured to receive a single finger, each of the plurality of finger slings being configured to be attached to a respective one of the plurality of lines, and each of the plurality of lines is configured to extend through a single, respective one of the plurality of loops, and wherein each of the plurality of loops is configured to locate one of the plurality of finger slings adjacent to a respective finger.

5. The splint of claim 2, wherein the at least one loop is one of a separate component from the arcuate extension that is fixed thereon or built directly on the arcuate extension such that the at least one loop and the arcuate extension are integral.

6. The splint of claim 1, wherein the main splint body further comprises straps that cooperate with buckles to secure the main splint body around the portion of the arm, wherein the dynamic traction attachment further comprises an insert that is configured to detachably attach to the straps such that arcuate extension covers a back of the hand that is opposite from a palm of the hand.

7. The splint of claim 6, wherein at least one of the straps comprises two layers, the insert being attached to the at least one strap by a portion of the insert being sandwiched between the two layers.

8. The splint of claim 7, wherein the insert comprises a projection configured to abut one of the straps thereby securing the insert in a longitudinal direction and locating the insert longitudinally, the line is attached to the projection.

9. The splint of claim 1, wherein a contour of the dynamic traction attachment is configured to be adjusted at least one of immediately prior to being attached to the main splint body and after being attached to the main splint body.

10. The splint of claim 9, wherein the contour of the dynamic traction attachment is configured to be adjusted after being heated.

11. The splint of claim 1, further comprising a hinge having first and second legs extending from a center portion thereof, the first leg configured to be positioned on a first splint portion that covers the portion of the forearm, the second leg configured to be positioned on a second splint portion that covers the first portion of the hand, the center portion configured to be positioned on a third splint portion that covers the wrist, the hinge being configured to lock the hand at various angles with respect to the forearm.

12. A method of providing a splint adapted for use on at least a portion of an arm of a person, the method further comprising the steps of:
    providing a main splint body configured to be positioned around the portion of the arm such that the splint extends longitudinally over: at least a portion of a forearm, over a wrist, and over a portion of a hand, the main splint body further comprising at least one pocket therein;
    providing a plurality of support inserts configured to be removably inserted into the at least one pocket, each of the plurality of support inserts having a contour that is configured to be adjusted at least one of immediately prior to being inserted into the at least one pocket and after being inserted into the at least one pocket such that the plurality of support inserts can be customized to the person;
    providing a dynamic traction attachment that is configured to detachably attach to the main splint body, the dynamic traction attachment comprising an arcuate extension fixed thereto, the arcuate extension configured to extend past a longitudinal end of the main splint body to cover a portion of some fingers of the hand on which the main splint body is positioned over; and attaching at least one finger sling to the dynamic traction attachment, wherein the arcuate extension is configured to locate the at least one finger sling adjacent to a finger of the hand on which the main splint body is positioned over such that the finger can be placed inside the at least one finger sling, wherein the at least one finger sling is attached to the dynamic traction attachment by a line, wherein a first line end is attached to the dynamic traction attachment and a second line end is attached to the at least one finger sling.

13. The method of claim 12, wherein the step of providing the plurality of support inserts further comprises the contour of each of the plurality of support inserts is configured to be adjusted after being heated.

14. The method of claim 13, further comprising the steps of:

inserting at least one of the plurality of support inserts into the at least one pocket of the main splint body;

after inserting the plurality of support inserts, heating the main splint body including the plurality of support inserts;

after heating the main splint body, positioning the main splint body on the portion of the arm such that the contour of each of the heated plurality of support inserts is adjusted based on the shape of at least one of the portion of the forearm, the wrist, and the portion of the hand of the person.

15. The method of claim 12, further comprising the step of:

providing a hinge having first and second legs extending from a center portion thereof, the first leg configured to be positioned on a first splint portion that covers the portion of the forearm, the second leg configured to be positioned on a second splint portion that covers the portion of the hand, the center portion configured to be positioned on a third splint portion that covers the wrist, the hinge being configured to lock the hand at various angles with respect to the forearm.

16. The method of claim 15, wherein the step of providing the hinge further comprises at least one of the first leg and the second leg having a hinge contour that is configured to be adjusted at least one of immediately prior to being positioned on the main splint body and after being positioned on the main splint body such that the hinge contour can be customized to the person.

17. The method of claim 12, further comprising the steps of:

heating at least one of the plurality of support inserts;

after heating the at least one of the plurality of support inserts, at least one of reshaping the at least one of the plurality of support inserts and adjusting the contour based on the nature of the person's injury;

inserting the at least one of the plurality of support inserts in the at least one pocket.

18. The method of claim 17, further comprising the step of:

providing a hinge having first and second legs extending from a center portion thereof, the first leg configured to be positioned on a first splint portion that covers the portion of the forearm, the second leg configured to be positioned on a second splint portion that covers the portion of the hand, the center portion configured to be positioned on a third splint portion that covers the wrist, the hinge being configured to lock the hand at various angles with respect to the forearm.

* * * * *